US012662531B2

(12) United States Patent
Jin et al.

(10) Patent No.: US 12,662,531 B2
(45) Date of Patent: Jun. 23, 2026

(54) CLDN18.2 ANTIBODY AND USE THEREOF

(71) Applicant: FUTUREGEN BIOPHARMACEUTICAL (BEIJING) CO., LTD., Beijing (CN)

(72) Inventors: Zhaoyu Jin, Beijing (CN); Yun Li, Beijing (CN); Feng Li, Beijing (CN); Naifan Huo, Beijing (CN); Xiumei Jin, Beijing (CN); Li Ren, Beijing (CN); Zhexian Yan, Beijing (CN)

(73) Assignee: FUTUREGEN BIOPHARMACEUTICAL (BEIJING) CO., LTD., Beijing (CN)

(*) Notice: Subject to any disclaimer, the term of this patent is extended or adjusted under 35 U.S.C. 154(b) by 1200 days.

(21) Appl. No.: 17/626,757

(22) PCT Filed: Jul. 10, 2020

(86) PCT No.: PCT/CN2020/101383
§ 371 (c)(1),
(2) Date: Jan. 12, 2022

(87) PCT Pub. No.: WO2021/008463
PCT Pub. Date: Jan. 21, 2021

(65) Prior Publication Data

US 2022/0235129 A1 Jul. 28, 2022

(30) Foreign Application Priority Data

Jul. 12, 2019 (CN) ......................... 201910628018.9

(51) Int. Cl.

| | |
|---|---|
| ***C07K 16/28*** | (2006.01) |
| ***A61P 35/00*** | (2006.01) |
| ***C07K 16/32*** | (2006.01) |
| *A61K 39/00* | (2006.01) |

(52) U.S. Cl.
CPC .............. *C07K 16/28* (2013.01); *A61P 35/00* (2018.01); *C07K 16/32* (2013.01); *A61K 2039/505* (2013.01); *C07K 2317/24* (2013.01); *C07K 2317/565* (2013.01); *C07K 2317/732* (2013.01); *C07K 2317/92* (2013.01)

(58) Field of Classification Search
CPC .... C07K 16/28; C07K 16/32; C07K 2317/24; C07K 2317/565; C07K 2317/732; C07K 2317/92; C07K 2317/21; C07K 2317/41; C07K 2317/734; C07K 2317/52; C07K 2317/56; C07K 2317/31; A61P 35/00; A61K 2039/505; A61K 39/3955; A61K 45/06; A61K 47/68; A61K 47/6801; A61K 47/6851; C12N 2510/00; C12N 2800/107; C12N 5/0686; C12N 15/85
See application file for complete search history.

(56) References Cited

U.S. PATENT DOCUMENTS 10,421,817 B1 * 9/2019 Hu .................... A61K 47/6801

FOREIGN PATENT DOCUMENTS

| | | | | |
|---|---|---|---|---|
| CN | 109172820 A | 1/2019 | | |
| CN | 109762067 A | 5/2019 | | |
| EP | 3099706 B1 | 10/2018 | | |
| JP | 2015522543 A | 8/2015 | | |
| KR | 20110084196 A | 7/2011 | | |
| WO | 2015113576 A1 | 8/2015 | | |
| WO | 2016180468 A1 | 11/2016 | | |
| WO | WO-2020082209 A1 * | 4/2020 | | ......... A61K 40/4202 |

OTHER PUBLICATIONS

Chen et al., "Advances in the application of claudins to tumor therapy", Chin J Biotech Jun. 25, 2019, 35(6): 931?941.
Tureci et al., "Claudin-18 gene structure, regulation, and expression is evolutionary conserved in mammals", Gene 481 (2011) 83-92.
Woll et al., "Claudin 18.2 is a target for IMAB362 antibody in pancreatic neoplasms", Int. J. Cancer: 134, 731-739 (2014).
Xu et al., "Advances of CLDN18.2 protein in the therapy of malignant tumors", Chin J Clin On col. 20 19. vol. 46. No. 6, 311-315.
Zhu et al., "Targeting CLDN18.2 by CD3 Bispecific and ADC Modalities for the Treatments of Gastric and Pancreatic Cancer", Scientific Reports | (2019) 9:8420.
Prabhsimranjot Singth et al., "Anti-claudin 18.2 antibody as new targeted therapy for advanced gastric cancer", Journal of Hematology & Oncology, vol. 10, pp. 1-5 (May 12, 2017).

* cited by examiner

*Primary Examiner* — Misook Yu
*Assistant Examiner* — Dennis Cherian George
(74) *Attorney, Agent, or Firm* — Lando & Anastasi, LLP

(57) ABSTRACT

Provided are a CLDN18.2-combined antibody and an unfucosylated form thereof. Further provided are a preparation method for the antibody, a conjugate, and a composition containing the antibody, and use thereof in the treatment of a disease such as cancer.

24 Claims, 17 Drawing Sheets

Specification includes a Sequence Listing.

FACS Binding

A

| | A1 | A2 | A3 | A4 | A5 |
|---|---|---|---|---|---|
| EC50 | 0.7021 | 12.73 | 1.473 | 0.923 | 0.4499 |

FACS Binding

B

| | A5F | A6F | IMAB362 |
|---|---|---|---|
| EC50 | 0.391 | 0.7877 | 1.431 |

A

B

| | Ka (1/Ms) | Kd (M) | KD | tc |
|---|---|---|---|---|
| 18.2-A1 | $1.276 \times 10^5$ | $8.482 \times 10^{-3}$ | $6.647 \times 10^{-8}$ | $2.717 \times 10^7$ |
| 18.2-A1F | $5.019 \times 10^5$ | $4.547 \times 10^{-3}$ | $9.06 \times 10^{-9}$ | $2.883 \times 10^8$ |

FcRgIIa Binding FACS：

ADCC Reporting Assay:

A

B

SEQUENCE LISTING

```
<160> NUMBER OF SEQ ID NOS: 64

<210> SEQ ID NO 1
<211> LENGTH: 118
<212> TYPE: PRT
<213> ORGANISM: Artificial Sequence
<220> FEATURE:
<223> OTHER INFORMATION: 18.2-A1 VH

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Leu Ile Trp Val Arg Gln Ala Pro Gly Gln Gly Leu Glu Trp Ile
        35                  40                  45

Gly Thr Ile Val Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Arg Thr Gly Asn Ser Phe Asp Tyr Trp Gly Gln Gly Thr
            100                 105                 110

Leu Val Thr Val Ser Ser
        115


<210> SEQ ID NO 2
<211> LENGTH: 354
<212> TYPE: DNA
<213> ORGANISM: Artificial Sequence
<220> FEATURE:
<223> OTHER INFORMATION: 18.2-A1 VH

<400> SEQUENCE: 2

gaggtccaac tcgttcaatc tggagcagag gtaaaaaagc ctggagccag cgtcaaggtt      60

agttgtaagg catctggtta cacctttacc agctcttggc tcatttgggt gcgccaggca     120

cctggtcagg gattggaatg gattggcact atcgtcccct ctgactctta caccaactac     180

aatcagaaat ttaaagatcg cgccactttg acagtcgata agtctacgag tacggcttat     240

atggagctca gttccctgcg cagcgaggac acagccgtct attactgcac ccgcttcagg     300

accggtaaca gctttgacta ctggggacaa ggtacattgg ttacggtcag ctct           354


<210> SEQ ID NO 3
<211> LENGTH: 5
<212> TYPE: PRT
```

-continued

<213> ORGANISM: Artificial Sequence
<220> FEATURE:
<223> OTHER INFORMATION: 18.2-A1 CDR H1

<400> SEQUENCE: 3

Ser Ser Trp Leu Ile
1               5

<210> SEQ ID NO 4
<211> LENGTH: 17
<212> TYPE: PRT
<213> ORGANISM: Artificial Sequence
<220> FEATURE:
<223> OTHER INFORMATION: 18.2-A1 CDR H2

<400> SEQUENCE: 4

Thr Ile Val Pro Ser Asp Ser Tyr Thr Asn Tyr Asn Gln Lys Phe Lys
1               5                   10                  15

Asp

<210> SEQ ID NO 5
<211> LENGTH: 9
<212> TYPE: PRT
<213> ORGANISM: Artificial Sequence
<220> FEATURE:
<223> OTHER INFORMATION: 18.2-A1 CDR H3

<400> SEQUENCE: 5

Phe Arg Thr Gly Asn Ser Phe Asp Tyr
1               5

<210> SEQ ID NO 6
<211> LENGTH: 113
<212> TYPE: PRT
<213> ORGANISM: Artificial Sequence
<220> FEATURE:
<223> OTHER INFORMATION: 18.2-A1 VL

<400> SEQUENCE: 6

Asp Ile Val Met Thr Gln Ser Pro Asp Ser Leu Ser Val Gly Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Val Ala Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ser Ile Ala Tyr Pro Phe Thr Phe Gly Gln Gly Thr Lys Val Glu Ile
            100                 105                 110

Lys

<210> SEQ ID NO 7
<211> LENGTH: 339
<212> TYPE: DNA
<213> ORGANISM: Artificial Sequence
<220> FEATURE:
<223> OTHER INFORMATION: 18.2-A1 VL

<400> SEQUENCE: 7

-continued

```
gacatcgtta tgactcagtc tcccgactcc ctcagcgtcg gcttgggtga acgcgccact     60

atcaattgta agtccagtca gtccgtcctc aattccggga atcagaagaa ctaccttaca    120

tggtatcagc agaaacctgg tcagccacca aaattgctca tctattgggc cgtggccagg    180

cagagcggcg tgcccgaccg ctttagtggg agcggctctg gcacagattt tacacttact    240

attagtagtc ttcaggccga ggatgtcgcg gtatattact gtcagaatag catagcctat    300

ccctttacct tcggtcaggg aacgaaggtt gaaatcaag                           339


<210> SEQ ID NO 8
<211> LENGTH: 17
<212> TYPE: PRT
<213> ORGANISM: Artificial Sequence
<220> FEATURE:
<223> OTHER INFORMATION: 18.2-A1 CDR L1

<400> SEQUENCE: 8

Lys Ser Ser Gln Ser Val Leu Asn Ser Gly Asn Gln Lys Asn Tyr Leu
1               5                   10                  15

Thr


<210> SEQ ID NO 9
<211> LENGTH: 7
<212> TYPE: PRT
<213> ORGANISM: Artificial Sequence
<220> FEATURE:
<223> OTHER INFORMATION: 18.2-A1 CDR L2

<400> SEQUENCE: 9

Trp Ala Val Ala Arg Gln Ser
1               5


<210> SEQ ID NO 10
<211> LENGTH: 9
<212> TYPE: PRT
<213> ORGANISM: Artificial Sequence
<220> FEATURE:
<223> OTHER INFORMATION: 18.2-A1 CDR L3

<400> SEQUENCE: 10

Gln Asn Ser Ile Ala Tyr Pro Phe Thr
1               5


<210> SEQ ID NO 11
<211> LENGTH: 118
<212> TYPE: PRT
<213> ORGANISM: Artificial Sequence
<220> FEATURE:
<223> OTHER INFORMATION: 18.2-A2 VH

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Val Gly Trp Val Arg Gln Ala Pro Gly Gln Gly Leu Glu Trp Ile
        35                  40                  45

Gly Asn Val Ser Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Thr Arg Leu Ser Ser Gly Asn Ser Phe Asp Tyr Trp Gly Gln Gly Thr
            100                 105                 110

Leu Val Thr Val Ser Ser
        115


<210> SEQ ID NO 12
<211> LENGTH: 354
<212> TYPE: DNA
<213> ORGANISM: Artificial Sequence
<220> FEATURE:
<223> OTHER INFORMATION: 18.2-A2 VH

<400> SEQUENCE: 12

gaggtccaac tcgttcaatc tggagcagag gtaaaaaagc ctggagccag cgtcaaggtt      60

agttgtaagg catctggtta cacctttacc agcttttggg tcggttgggt gcgccaggca     120

cctggtcagg gattggaatg gattggcaat gtctccccct ctgactctta caccaactac     180

aatcagaaat ttaaagatcg cgccactttg acagtcgata agtctacgag tacggcttat     240

atggagctca gttccctgcg cagcgaggac acagccgtct attactgcac ccgcttatca     300

agcggtaaca gctttgacta ctggggacaa ggtacattgg ttacggtcag ctct           354


<210> SEQ ID NO 13
<211> LENGTH: 5
<212> TYPE: PRT
<213> ORGANISM: Artificial Sequence
<220> FEATURE:
<223> OTHER INFORMATION: 18.2-A2 CDR H1

<400> SEQUENCE: 13

Ser Phe Trp Val Gly
1               5


<210> SEQ ID NO 14
<211> LENGTH: 17
<212> TYPE: PRT
<213> ORGANISM: Artificial Sequence
<220> FEATURE:
<223> OTHER INFORMATION: 18.2-A2 CDR H2

<400> SEQUENCE: 14

Asn Val Ser Pro Ser Asp Ser Tyr Thr Asn Tyr Asn Gln Lys Phe Lys
1               5                   10                  15

Asp


<210> SEQ ID NO 15
<211> LENGTH: 9
<212> TYPE: PRT
<213> ORGANISM: Artificial Sequence
<220> FEATURE:
<223> OTHER INFORMATION: 18.2-A2 CDR H3

<400> SEQUENCE: 15

Leu Ser Ser Gly Asn Ser Phe Asp Tyr
1               5


<210> SEQ ID NO 16
<211> LENGTH: 113
<212> TYPE: PRT
<213> ORGANISM: Artificial Sequence
<220> FEATURE:
<223> OTHER INFORMATION: 18.2-A2 VL
```

<400> SEQUENCE: 16

Asp Ile Val Met Thr Gln Ser Pro Asp Ser Leu Ser Val Ser Leu Gly
1 5 10 15

Glu Arg Ala Thr Ile Asn Cys Lys Ser Ser Gln Ser Val Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ser Ser Thr Lys Gln Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ala Phe Ser Phe Pro Phe Thr Phe Gly Gln Gly Thr Lys Val Glu Ile
100 105 110

Lys

<210> SEQ ID NO 17
<211> LENGTH: 339
<212> TYPE: DNA
<213> ORGANISM: Artificial Sequence
<220> FEATURE:
<223> OTHER INFORMATION: 18.2-A2 VL

<400> SEQUENCE: 17
gacatcgtta tgactcagtc tcccgactcc ctcagcgtca gcttgggtga acgcgccact 60
atcaattgta agtccagtca gtccgtcctc aattccggga atcagaagaa ctaccttaca 120
tggtatcagc agaaacctgg tcagccacca aaattgctca tctattggag ctcgaccaag 180
cagagcggcg tgcccgaccg ctttagtggg agcggctctg gcacagattt tacacttact 240
attagtagtc ttcaggccga ggatgtcgcg gtatattact gtcagaatgc cttttcgttc 300
ccctttacct tcggtcaggg aacgaaggtt gaaatcaag 339

<210> SEQ ID NO 18
<211> LENGTH: 17
<212> TYPE: PRT
<213> ORGANISM: Artificial Sequence
<220> FEATURE:
<223> OTHER INFORMATION: 18.2-A2 CDR L1

<400> SEQUENCE: 18

Lys Ser Ser Gln Ser Val Leu Asn Ser Gly Asn Gln Lys Asn Tyr Leu
1 5 10 15

Thr

<210> SEQ ID NO 19
<211> LENGTH: 7
<212> TYPE: PRT
<213> ORGANISM: Artificial Sequence
<220> FEATURE:
<223> OTHER INFORMATION: 18.2-A2 CDR L2

<400> SEQUENCE: 19

Trp Ser Ser Thr Lys Gln Ser
1 5

<210> SEQ ID NO 20
<211> LENGTH: 9

<212> TYPE: PRT
<213> ORGANISM: Artificial Sequence
<220> FEATURE:
<223> OTHER INFORMATION: 18.2-A2 CDR L3

<400> SEQUENCE: 20

Gln Asn Ala Phe Ser Phe Pro Phe Thr
1               5

<210> SEQ ID NO 21
<211> LENGTH: 118
<212> TYPE: PRT
<213> ORGANISM: Artificial Sequence
<220> FEATURE:
<223> OTHER INFORMATION: 18.2-A3 VH

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Leu Asn Trp Val Arg Gln Ala Pro Gly Gln Gly Leu Glu Trp Ile
        35                  40                  45

Gly Ser Met Tyr Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Ser Arg Gly Asn Ser Phe Asp Tyr Trp Gly Gln Gly Thr
            100                 105                 110

Leu Val Thr Val Ser Ser
        115

<210> SEQ ID NO 22
<211> LENGTH: 354
<212> TYPE: DNA
<213> ORGANISM: Artificial Sequence
<220> FEATURE:
<223> OTHER INFORMATION: 18.2-A3 VH

<400> SEQUENCE: 22
gaggtccaac tcgttcaatc tggagcagag gtaaaaaagc ctggagccag cgtcaaggtt 60
agttgtaagg catctggtta cacctttacc agctattggc tcaattgggt gcgccaggca 120
cctggtcagg gattggaatg gattggcagt atgtatccct ctgactctta caccaactac 180
aatcagaaat ttaaagatcg cgccactttg acagtcgata agtctacgag tacggcttat 240
atggagctca gttccctgcg cagcgaggac acagccgtct attactgcac ccgcttcagc 300
cgcggcaaca gctttgacta ctggggacaa ggtacattgg ttacggtcag ctct 354

<210> SEQ ID NO 23
<211> LENGTH: 5
<212> TYPE: PRT
<213> ORGANISM: Artificial Sequence
<220> FEATURE:
<223> OTHER INFORMATION: 18.2-A3 CDR H1

<400> SEQUENCE: 23

Ser Tyr Trp Leu Asn
1               5

<210> SEQ ID NO 24
<211> LENGTH: 17
<212> TYPE: PRT
<213> ORGANISM: Artificial Sequence
<220> FEATURE:
<223> OTHER INFORMATION: 18.2-A3 CDR H2

<400> SEQUENCE: 24

Ser Met Tyr Pro Ser Asp Ser Tyr Thr Asn Tyr Asn Gln Lys Phe Lys
1               5                   10                  15

Asp

<210> SEQ ID NO 25
<211> LENGTH: 9
<212> TYPE: PRT
<213> ORGANISM: Artificial Sequence
<220> FEATURE:
<223> OTHER INFORMATION: 18.2-A3 CDR H3

<400> SEQUENCE: 25

Phe Ser Arg Gly Asn Ser Phe Asp Tyr
1               5

<210> SEQ ID NO 26
<211> LENGTH: 113
<212> TYPE: PRT
<213> ORGANISM: Artificial Sequence
<220> FEATURE:
<223> OTHER INFORMATION: 18.2-A3 VL

<400> SEQUENCE: 26

Asp Ile Val Met Thr Gln Ser Pro Asp Ser Leu Thr Val Ala Leu Gly
1               5                   10                  15

Glu Arg Ala Thr Ile Asn Cys Lys Ser Ser Gln Ser Leu Leu Glu Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Trp Ala Lys Asn Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ala Phe Pro Phe Thr Phe Gly Gln Gly Thr Lys Val Glu Ile
            100                 105                 110

Lys

<210> SEQ ID NO 27
<211> LENGTH: 339
<212> TYPE: DNA
<213> ORGANISM: Artificial Sequence
<220> FEATURE:
<223> OTHER INFORMATION: 18.2-A3 VL

<400> SEQUENCE: 27
gacatcgtta tgactcagtc tcccgactcc ctcaccgtcg ccttgggtga acgcgccact      60
atcaattgta agtccagtca gtccctcctc gagtccggga atcagaagaa ctaccttaca     120
tggtatcagc agaaacctgg tcagccacca aaattgctca tctattggag ctgggccaag     180
aatagcggcg tgcccgaccg ctttagtggg agcggctctg gcacagattt tacacttact     240

```
attagtagtc ttcaggccga ggatgtcgcg gtatattact gtcagaatgc ttatgcattt    300

ccctttacct tcggtcaggg aacgaaggtt gaaatcaag                           339


<210> SEQ ID NO 28
<211> LENGTH: 17
<212> TYPE: PRT
<213> ORGANISM: Artificial Sequence
<220> FEATURE:
<223> OTHER INFORMATION: 18.2-A3 CDR L1

<400> SEQUENCE: 28

Lys Ser Ser Gln Ser Leu Leu Glu Ser Gly Asn Gln Lys Asn Tyr Leu
1               5                   10                  15

Thr


<210> SEQ ID NO 29
<211> LENGTH: 7
<212> TYPE: PRT
<213> ORGANISM: Artificial Sequence
<220> FEATURE:
<223> OTHER INFORMATION: 18.2-A3 CDR L2

<400> SEQUENCE: 29

Trp Ser Trp Ala Lys Asn Ser
1               5


<210> SEQ ID NO 30
<211> LENGTH: 9
<212> TYPE: PRT
<213> ORGANISM: Artificial Sequence
<220> FEATURE:
<223> OTHER INFORMATION: 18.2-A3 CDR L3

<400> SEQUENCE: 30

Gln Asn Ala Tyr Ala Phe Pro Phe Thr
1               5


<210> SEQ ID NO 31
<211> LENGTH: 118
<212> TYPE: PRT
<213> ORGANISM: Artificial Sequence
<220> FEATURE:
<223> OTHER INFORMATION: 18.2-A4 VH

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Ser Trp Val Arg Gln Ala Pro Gly Gln Gly Leu Glu Trp Ile
        35                  40                  45

Gly Asn Ile Leu Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Trp Arg Gly Asn Ser Phe Asp Tyr Trp Gly Gln Gly Thr
            100                 105                 110

Leu Val Thr Val Ser Ser
        115
```

<210> SEQ ID NO 32
<211> LENGTH: 354
<212> TYPE: DNA
<213> ORGANISM: Artificial Sequence
<220> FEATURE:
<223> OTHER INFORMATION: 18.2-A4 VH

<400> SEQUENCE: 32
gaggtccaac tcgttcaatc tggagcagag gtaaaaaagc ctggagccag cgtcaaggtt 60
agttgtaagg catctggtta cacctttacc agcttttgga tcagttgggt gcgccaggca 120
cctggtcagg gattggaatg gattggcaac attctcccct ctgactctta caccaactac 180
aatcagaaat ttaaagatcg cgccactttg acagtcgata agtctacgag tacggcttat 240
atggagctca gttccctgcg cagcgaggac acagccgtct attactgcac ccgctactgg 300
cgcggcaaca gctttgacta ctggggacaa ggtacattgg ttacggtcag ctct 354

<210> SEQ ID NO 33
<211> LENGTH: 5
<212> TYPE: PRT
<213> ORGANISM: Artificial Sequence
<220> FEATURE:
<223> OTHER INFORMATION: 18.2-A4 CDR H1

<400> SEQUENCE: 33

Ser Phe Trp Ile Ser
1 5

<210> SEQ ID NO 34
<211> LENGTH: 17
<212> TYPE: PRT
<213> ORGANISM: Artificial Sequence
<220> FEATURE:
<223> OTHER INFORMATION: 18.2-A4 CDR H2

<400> SEQUENCE: 34

Asn Ile Leu Pro Ser Asp Ser Tyr Thr Asn Tyr Asn Gln Lys Phe Lys
1 5 10 15

Asp

<210> SEQ ID NO 35
<211> LENGTH: 9
<212> TYPE: PRT
<213> ORGANISM: Artificial Sequence
<220> FEATURE:
<223> OTHER INFORMATION: 18.2-A4 CDR H3

<400> SEQUENCE: 35

Tyr Trp Arg Gly Asn Ser Phe Asp Tyr
1 5

<210> SEQ ID NO 36
<211> LENGTH: 113
<212> TYPE: PRT
<213> ORGANISM: Artificial Sequence
<220> FEATURE:
<223> OTHER INFORMATION: 18.2-A4 VL

<400> SEQUENCE: 36

Asp Ile Val Met Thr Gln Ser Pro Asp Ser Leu Ala Leu Ala Leu Gly
1 5 10 15

Glu Arg Ala Thr Ile Asn Cys Lys Ser Ser Gln Ser Ile Ile Asn Ser
20 25 30

-continued

Gly Asn Gln Lys Asn Tyr Leu Thr Trp Tyr Gln Gln Lys Pro Gly Gln
        35                  40                  45

Pro Pro Lys Leu Leu Ile Tyr Trp Gly Gly Thr Arg His Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Gly Tyr Tyr Ser Pro Phe Thr Phe Gly Gln Gly Thr Lys Val Glu Ile
            100                 105                 110

Lys

<210> SEQ ID NO 37
<211> LENGTH: 339
<212> TYPE: DNA
<213> ORGANISM: Artificial Sequence
<220> FEATURE:
<223> OTHER INFORMATION: 18.2-A4 VL

<400> SEQUENCE: 37
gacatcgtta tgactcagtc tcccgactcc ctcgccctcg ccttgggtga acgcgccact     60
atcaattgta agtccagtca gtccatcatc aattccggga atcagaagaa ctaccttaca    120
tggtatcagc agaaacctgg tcagccacca aaattgctca tctattgggg cgggaccagg    180
catagcggcg tgcccgaccg ctttagtggg agcggctctg gcacagattt tacacttact    240
attagtagtc ttcaggccga ggatgtcgcg gtatattact gtcagaatgg ctattactct    300
ccctttacct tcggtcaggg aacgaaggtt gaaatcaag                           339

<210> SEQ ID NO 38
<211> LENGTH: 17
<212> TYPE: PRT
<213> ORGANISM: Artificial Sequence
<220> FEATURE:
<223> OTHER INFORMATION: 18.2-A4 CDR L1

<400> SEQUENCE: 38

Lys Ser Ser Gln Ser Ile Ile Asn Ser Gly Asn Gln Lys Asn Tyr Leu
1               5                   10                  15

Thr

<210> SEQ ID NO 39
<211> LENGTH: 7
<212> TYPE: PRT
<213> ORGANISM: Artificial Sequence
<220> FEATURE:
<223> OTHER INFORMATION: 18.2-A4 CDR L2

<400> SEQUENCE: 39

Trp Gly Gly Thr Arg His Ser
1               5

<210> SEQ ID NO 40
<211> LENGTH: 9
<212> TYPE: PRT
<213> ORGANISM: Artificial Sequence
<220> FEATURE:
<223> OTHER INFORMATION: 18.2-A4 CDR L3

<400> SEQUENCE: 40

Gln Asn Gly Tyr Tyr Ser Pro Phe Thr
1               5

<210> SEQ ID NO 41
<211> LENGTH: 118
<212> TYPE: PRT
<213> ORGANISM: Artificial Sequence
<220> FEATURE:
<223> OTHER INFORMATION: 18.2-A5 VH

<400> SEQUENCE: 41

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Val Gly Trp Val Arg Gln Ala Pro Gly Gln Gly Leu Glu Trp Ile
        35                  40                  45

Gly Asn Ser Tyr Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Gly Arg Gly Asn Ser Phe Asp Tyr Trp Gly Gln Gly Thr
            100                 105                 110

Leu Val Thr Val Ser Ser
        115
```

<210> SEQ ID NO 42
<211> LENGTH: 354
<212> TYPE: DNA
<213> ORGANISM: Artificial Sequence
<220> FEATURE:
<223> OTHER INFORMATION: 18.2-A5 VH

<400> SEQUENCE: 42

```
gaggtccaac tcgttcaatc tggagcagag gtaaaaaagc ctggagccag cgtcaaggtt      60

agttgtaagg catctggtta cacctttacc agctcttggg tcggttgggt gcgccaggca     120

cctggtcagg gattggaatg gattggcaat agctacccct ctgactctta caccaactac     180

aatcagaaat ttaaagatcg cgccactttg acagtcgata agtctacgag tacggcttat     240

atggagctca gttccctgcg cagcgaggac acagccgtct attactgcac ccgcttgggg     300

cgcggcaaca gctttgacta ctggggacaa ggtacattgg ttacggtcag ctct           354
```

<210> SEQ ID NO 43
<211> LENGTH: 5
<212> TYPE: PRT
<213> ORGANISM: Artificial Sequence
<220> FEATURE:
<223> OTHER INFORMATION: 18.2-A5 CDR H1

<400> SEQUENCE: 43

```
Ser Ser Trp Val Gly
1               5
```

<210> SEQ ID NO 44
<211> LENGTH: 17
<212> TYPE: PRT
<213> ORGANISM: Artificial Sequence
<220> FEATURE:
<223> OTHER INFORMATION: 18.2-A5 CDR H2

<400> SEQUENCE: 44

Asn Ser Tyr Pro Ser Asp Ser Tyr Thr Asn Tyr Asn Gln Lys Phe Lys
1 5 10 15

Asp

<210> SEQ ID NO 45
<211> LENGTH: 9
<212> TYPE: PRT
<213> ORGANISM: Artificial Sequence
<220> FEATURE:
<223> OTHER INFORMATION: 18.2-A5 CDR H3

<400> SEQUENCE: 45

Leu Gly Arg Gly Asn Ser Phe Asp Tyr
1 5

<210> SEQ ID NO 46
<211> LENGTH: 113
<212> TYPE: PRT
<213> ORGANISM: Artificial Sequence
<220> FEATURE:
<223> OTHER INFORMATION: 18.2-A5 VL

<400> SEQUENCE: 46

Asp Ile Val Met Thr Gln Ser Pro Asp Ser Leu Thr Val Ala Leu Gly
1 5 10 15

Glu Arg Ala Thr Ile Asn Cys Lys Ser Ser Gln Ser Leu Ile His Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Gly Leu Ser Lys Asn Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ser Ile Tyr Tyr Pro Phe Thr Phe Gly Gln Gly Thr Lys Val Glu Ile
100 105 110

Lys

<210> SEQ ID NO 47
<211> LENGTH: 339
<212> TYPE: DNA
<213> ORGANISM: Artificial Sequence
<220> FEATURE:
<223> OTHER INFORMATION: 18.2-A5 VL

<400> SEQUENCE: 47
gacatcgtta tgactcagtc tcccgactcc ctcaccgtcg ccttgggtga acgcgccact 60
atcaattgta agtccagtca gtccctcatc cattccggga atcagaagaa ctaccttaca 120
tggtatcagc agaaacctgg tcagccacca aaattgctca tctattgggg cttgagcaag 180
aatagcggcg tgcccgaccg ctttagtggg agcggctctg gcacagattt tacacttact 240
attagtagtc ttcaggccga ggatgtcgcg gtatattact gtcagaatag catttactat 300
ccctttacct tcggtcaggg aacgaaggtt gaaatcaag 339

<210> SEQ ID NO 48
<211> LENGTH: 17
<212> TYPE: PRT
<213> ORGANISM: Artificial Sequence

<220> FEATURE:
<223> OTHER INFORMATION: 18.2-A5 CDR L1

<400> SEQUENCE: 48

Lys Ser Ser Gln Ser Leu Ile His Ser Gly Asn Gln Lys Asn Tyr Leu
1 5 10 15

Thr

<210> SEQ ID NO 49
<211> LENGTH: 7
<212> TYPE: PRT
<213> ORGANISM: Artificial Sequence
<220> FEATURE:
<223> OTHER INFORMATION: 18.2-A5 CDR L2

<400> SEQUENCE: 49

Trp Gly Leu Ser Lys Asn Ser
1 5

<210> SEQ ID NO 50
<211> LENGTH: 9
<212> TYPE: PRT
<213> ORGANISM: Artificial Sequence
<220> FEATURE:
<223> OTHER INFORMATION: 18.2-A5 CDR L3

<400> SEQUENCE: 50

Gln Asn Ser Ile Tyr Tyr Pro Phe Thr
1 5

<210> SEQ ID NO 51
<211> LENGTH: 330
<212> TYPE: PRT
<213> ORGANISM: Artificial Sequence
<220> FEATURE:
<223> OTHER INFORMATION: Heavy Chain Constant Region

<400> SEQUENCE: 51

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 52
<211> LENGTH: 993
<212> TYPE: DNA
<213> ORGANISM: Artificial Sequence
<220> FEATURE:
<223> OTHER INFORMATION: Heavy Chain Constant Region

<400> SEQUENCE: 52

```
gcgagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgact gtgccctcta gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaagag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa tga                                 993
```

<210> SEQ ID NO 53
<211> LENGTH: 107
<212> TYPE: PRT
<213> ORGANISM: Artificial Sequence

<220> FEATURE:
<223> OTHER INFORMATION: ????????

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 54
<211> LENGTH: 324
<212> TYPE: DNA
<213> ORGANISM: Artificial Sequence
<220> FEATURE:
<223> OTHER INFORMATION: Light Chain Constant Region

<400> SEQUENCE: 54
cggaccgtgg cagcaccaag tgtcttcatc ttcccgccat ctgatgagca gttgaaatct 60
ggaactgctt ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg ttaa 324

<210> SEQ ID NO 55
<211> LENGTH: 118
<212> TYPE: PRT
<213> ORGANISM: Artificial Sequence
<220> FEATURE:
<223> OTHER INFORMATION: 18.2-A6 VH

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Leu Gly Trp Val Arg Gln Ala Pro Gly Gln Gly Leu Glu Trp Ile
        35                  40                  45

Gly Ile Ile Tyr Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Trp Arg Gly Asn Ser Phe Asp Tyr Trp Gly Gln Gly Thr
            100                 105                 110

Leu Val Thr Val Ser Ser
115

<210> SEQ ID NO 56
<211> LENGTH: 354
<212> TYPE: DNA
<213> ORGANISM: Artificial Sequence
<220> FEATURE:
<223> OTHER INFORMATION: 18.2-A6 VH

<400> SEQUENCE: 56
gaggtccaac tcgttcaatc tggagcagag gtaaaaaagc ctggagccag cgtcaaggtt 60
agttgtaagg catctggtta cacctttacc agctattggc tcggttgggt gcgccaggca 120
cctggtcagg gattggaatg gattggcatt atatacccct ctgactctta caccaactac 180
aatcagaaat ttaaagatcg cgccactttg acagtcgata agtctacgag tacggcttat 240
atggagctca gttccctgcg cagcgaggac acagccgtct attactgcac ccgcttctgg 300
cgcggtaaca gctttgacta ctggggacaa ggtacattgg ttacggtcag ctct 354

<210> SEQ ID NO 57
<211> LENGTH: 5
<212> TYPE: PRT
<213> ORGANISM: Artificial Sequence
<220> FEATURE:
<223> OTHER INFORMATION: 18.2-A6 CDR H1

<400> SEQUENCE: 57

Ser Tyr Trp Leu Gly
1 5

<210> SEQ ID NO 58
<211> LENGTH: 17
<212> TYPE: PRT
<213> ORGANISM: Artificial Sequence
<220> FEATURE:
<223> OTHER INFORMATION: 18.2-A6 CDR H2

<400> SEQUENCE: 58

Ile Ile Tyr Pro Ser Asp Ser Tyr Thr Asn Tyr Asn Gln Lys Phe Lys
1 5 10 15

Asp

<210> SEQ ID NO 59
<211> LENGTH: 9
<212> TYPE: PRT
<213> ORGANISM: Artificial Sequence
<220> FEATURE:
<223> OTHER INFORMATION: 18.2-A6 CDR H3

<400> SEQUENCE: 59

Phe Trp Arg Gly Asn Ser Phe Asp Tyr
1 5

<210> SEQ ID NO 60
<211> LENGTH: 113
<212> TYPE: PRT
<213> ORGANISM: Artificial Sequence
<220> FEATURE:
<223> OTHER INFORMATION: 18.2-A6 VL

<400> SEQUENCE: 60

Asp Ile Val Met Thr Gln Ser Pro Asp Ser Leu Thr Ile Gly Leu Gly
1 5 10 15

-continued

```
Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ala Gly Lys Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Gly Tyr Ser His Pro Phe Thr Phe Gly Gln Gly Thr Lys Val Glu Ile
            100                 105                 110

Lys


<210> SEQ ID NO 61
<211> LENGTH: 339
<212> TYPE: DNA
<213> ORGANISM: Artificial Sequence
<220> FEATURE:
<223> OTHER INFORMATION: 18.2-A6 VL

<400> SEQUENCE: 61

gacatcgtta tgactcagtc tcccgactcc ctcaccatcg gcttgggtga acgcgccact     60

atcaattgta agtccagtca gtccctcctc aattccggga atcagaagaa ctaccttaca    120

tggtatcagc agaaacctgg tcagccacca aaattgctca tctattgggc cgcgggcaag    180

gagagcggcg tgcccgaccg ctttagtggg agcggctctg gcacagattt tacacttact    240

attagtagtc ttcaggccga ggatgtcgcg gtatattact gtcagaacgg gtattcccat    300

ccctttacct tcggtcaggg aacgaaggtt gaaatcaag                           339


<210> SEQ ID NO 62
<211> LENGTH: 17
<212> TYPE: PRT
<213> ORGANISM: Artificial Sequence
<220> FEATURE:
<223> OTHER INFORMATION: 18.2-A6 CDR L1

<400> SEQUENCE: 62

Lys Ser Ser Gln Ser Leu Leu Glu Ser Gly Asn Gln Lys Asn Tyr Leu
1               5                   10                  15

Thr


<210> SEQ ID NO 63
<211> LENGTH: 7
<212> TYPE: PRT
<213> ORGANISM: Artificial Sequence
<220> FEATURE:
<223> OTHER INFORMATION: 18.2-A6 CDR L2

<400> SEQUENCE: 63

Trp Ala Ala Gly Lys Glu Ser
1               5


<210> SEQ ID NO 64
<211> LENGTH: 9
<212> TYPE: PRT
<213> ORGANISM: Artificial Sequence
<220> FEATURE:
<223> OTHER INFORMATION: 18.2-A6 CDR L3
```

-continued

<400> SEQUENCE: 64

Gln Asn Gly Tyr Ser His Pro Phe Thr
1               5

CLDN18.2 ANTIBODY AND USE THEREOF

The present application is a U.S. National Stage Application under 35 U.S.C. § 371 of International Application No. PCT/CN2020/101383, filed Jul. 10, 2020, which claims priority to the Chinese Patent Application with the Application No. CN 201910628018.9 and the title of "CLDN18.2 Antibodies and Uses Thereof" filed on Jul. 12, 2019. The disclosure each of the aforementioned applications is incorporated herein by reference in their entirety as part of the present application.

SEQUENCE LISTING

The instant application contains a Sequence Listing which has been submitted electronically in ASCII format and is hereby incorporated by reference in its entirety. Said ASCII copy, created on Jan. 10, 2022, is named F2131-7000US_C20W7116-new-sequence-listing-20220110.txt and is 33,656 bytes in size.

FIELD OF THE INVENTION

The present disclosure relates to the field of immunotherapy. Specifically, the present disclosure relates to antibodies that bind to CLDN18.2 and defucosylated forms thereof, as well as uses of the antibodies in the treatment of diseases, especially in cancers.

BACKGROUND OF THE INVENTION

Upper gastrointestinal tumors, including gastric cancer and esophageal cancer, are common malignant tumors with poor prognosis worldwide. Gastric cancer particularly has a high occurrence in China, and nearly 42% of the new cases of gastric cancer in the world occurred in China. Due to the lack of early diagnosis, about 80% of gastric cancer patients are already at an advanced stage when they are diagnosed. As gastric cancer is not sensitive to conventional chemotherapeutic drugs, the five-year survival rate of patients with advanced gastric cancer is extremely low, and it has become the third leading cause of death in China. Therefore, the researches in recent years were dedicated to seeking for targeting therapies specific for gastric cancer.

Claudin family proteins are the main components of the tight junction structure that is widely distributed in epithelial cells. Similar to the structures of other proteins of Claudin family, CLDN18.2 is a membrane protein with a molecular weight of about 27.8 kd, which has four transmembrane regions and two relatively short extracellular regions (EC1 and EC2). Unlike other proteins of Claudin family, in normal tissue, CLDN18.2 is very specifically expressed only in the highly differentiated epithelial cells of the stomach (Tureci O et al., Gene, 2011). In tumors derived from gastric epithelial cells, a high proportion of tumor cells express CLDN18.2 on the surface. In the lymph nodes and other tissue metastases from gastric cancer cells, high levels of CLDN18.2 expression can also be detected (Woll S. et al., Int. J. Cancer, 2013). In addition to gastric cancer, CLDN18.2 is also expressed in a high proportion of tumor cells from cholangiocarcinoma, esophageal cancer, pancreatic cancer and the like. As a specific surface marker, CLDN18.2 has become a potential target for cancer treatment. The development of highly efficient antibody drugs against CLDN18.2 will provide the possibility for the treatment of a variety of cancers with great application potential and market value.

One of the main mechanisms of action of therapeutic monoclonal antibodies killing tumor cells is the ADCC effect (antibody dependent cell mediated cytotoxicity). After the antigen recognition segments (Fab) of a therapeutic antibody binds to the specific antigen on the surface of tumor cells, the cytocidal activity of the effector cells is activated by the binding of the antibody constant region (Fc) to the effector cells expressing the FC receptors (FcγR), resulting in the secretion of cytotoxic mediators including granzyme and perforin and the like, which ultimately leads to the lysis and destruction of target cells (tumor cells). The strength of an antibody binding to an antigen, the abundance of antigen expression and the strength of binding of antibody's FC region to FC receptors on the surface of effector cells can affect the intensity of the ADCC effect and thus the therapeutic effect against cancers (Jefferis and Lund, 2002).

SUMMARY OF THE INVENTION

The present disclosure provides novel anti-CLDN18.2 antibodies. The above antibodies can bind to CLDN18.2 with high affinity and specificity, and mediate the killing of CLDN18.2-expressing target cells (e.g., tumor cells) by effector cells. In addition, defucosylated forms of the above antibodies was generated, which can better bind to FcγRIIa and induce ADCC effect than unmodified antibodies.

Accordingly, in one aspect, the present disclosure relates to an antibody that binds to CLDN18.2 or an antigen-binding fragment thereof, wherein the antibody has the following heavy chain CDRs (CDRHs) and light chain CDRs (CDRLs):

a. CDRH1, CDRH2 and CDRH3 in a heavy chain variable region (VH) as shown in SEQ ID NO: 1; and CDRL1, CDRL2 and CDRL3 in a light chain variable region (VL) as shown in SEQ ID NO: 6;
b. CDRH1, CDRH2 and CDRH3 in a VH as shown in SEQ ID NO: 11; and CDRL1, CDRL2 and CDRL3 in a VL as shown in SEQ ID NO: 16;
c. CDRH1, CDRH2 and CDRH3 in a VH as shown in SEQ ID NO: 21; and CDRL1, CDRL2 and CDRL3 in a VL as shown in SEQ ID NO: 26;
d. CDRH1, CDRH2 and CDRH3 in a VH as shown in SEQ ID NO: 31; and CDRL1, CDRL2 and CDRL3 in a VL as shown in SEQ ID NO: 36;
e. CDRH1, CDRH2 and CDRH3 in a VH as shown in SEQ ID NO: 41; and CDRL1, CDRL2 and CDRL3 in a VL as shown in SEQ ID NO: 46; or
f. CDRH1, CDRH2 and CDRH3 in a VH as shown in SEQ ID NO: 55; and CDRL1, CDRL2 and CDRL3 in a VL as shown in SEQ ID NO: 60.

In some embodiments of the antibody or antigen-binding fragment thereof of the present disclosure, wherein the antibody has the following CDRHs and CDRLs:

a. CDRH1, CDRH2 and CDRH3 as shown in SEQ ID NOs: 3-5; and CDRL1, CDRL2 and CDRL3 as shown in SEQ ID NOs: 8-10;
b. CDRH1, CDRH2 and CDRH3 as shown in SEQ ID NOs: 13-15; and CDRL1, CDRL2 and CDRL3 as shown in SEQ ID NOs: 18-20;
c. CDRH1, CDRH2 and CDRH3 as shown in SEQ ID NOs: 23-25; and CDRL1, CDRL2 and CDRL3 as shown in SEQ ID NOs: 28-30;
d. CDRH1, CDRH2 and CDRH3 as shown in SEQ ID NOs: 33-35; and CDRL1, CDRL2 and CDRL3 as shown in SEQ ID NOs: 38-40;

e. CDRH1, CDRH2 and CDRH3 as shown in SEQ ID NOs: 43-45; and CDRL1, CDRL2 and CDRL3 as shown in SEQ ID NOs: 48-50; or f. CDRH1, CDRH2 and CDRH3 as shown in SEQ ID NOs: 57-59; and CDRL1, CDRL2 and CDRL3 as shown in SEQ ID NOs: 62-64.

In some embodiments of the antibody or antigen-binding fragment thereof of the present disclosure, wherein the antibody has the following VH and VL:

a. a VH comprising the amino acid sequence of SEQ ID NO: 1, and a VL comprising the amino acid sequence of SEQ ID NO: 6;

b. a VH comprising the amino acid sequence of SEQ ID NO: 11, and a VL comprising the amino acid sequence of SEQ ID NO: 16;

c. a VH comprising the amino acid sequence of SEQ ID NO: 21, and a VL comprising the amino acid sequence of SEQ ID NO: 26;

d. a VH comprising the amino acid sequence of SEQ ID NO: 31, and a VL comprising the amino acid sequence of SEQ ID NO: 36;

e. a VH comprising the amino acid sequence of SEQ ID NO: 41, and a VL comprising the amino acid sequence of SEQ ID NO: 46;

f. a VH comprising the amino acid sequence of SEQ ID NO: 55, and a VL comprising the amino acid sequence of SEQ ID NO: 60.

In some embodiments of the antibody or antigen-binding fragment thereof of the present disclosure, the antibody may have a heavy chain constant region sequence as shown in SEQ ID NO: 51 and/or a light chain constant region sequence as shown in SEQ ID NO: 53.

In some embodiments of the antibody or antigen-binding fragment thereof of the present disclosure, the antibody has an Fc region. In some embodiments, the antibody may have a glycosyl structure modification at Asn297, wherein the numbering is according to the EU numbering system. In some embodiments, the ratio of the glycosyl structure having fucose in the glycosyl structure is 50% or less. In some embodiments, the ratio of the glycosyl structure having fucose in the glycosyl structure is 30% or less, for example 20% or less, 10% or less, 5% or less, 2% or less, or 1% or less.

In a preferred embodiment, the ratio of the glycosyl structure having fucose in the antibody is 0%-1%.

In some embodiments of the antibody or antigen-binding fragment thereof of the present disclosure, the antibody is produced by a cell with Fut8 gene knockout. In some embodiments, the cell may be selected from a CHO cell and a HEK293 cell.

In some embodiments of the antibody or antigen-binding fragment thereof of the present disclosure, the antibody has an increased FcγRIIIa binding activity as compared to an antibody produced in a cell without Fut8 gene knockout. In some embodiments, the antibody has an increased ADCC activity as compared to an antibody produced in a cell without Fut8 gene knockout.

In some embodiments of the antibody or antigen-binding fragment thereof of the present disclosure, the antibody may be a monoclonal antibody. In other embodiments, the antibody may be a bispecific antibody or a multispecific antibody.

In some embodiments of the antibody or antigen-binding fragment thereof of the present disclosure, the antibody may be selected from a group consisting of IgG, IgA, IgM, IgE, and IgD isotypes. In some embodiments, the antibody may be selected from a group consisting of IgG1, IgG2, IgG3, and IgG4 subclasses.

In any embodiment of an antibody or antigen-binding fragment thereof of the present disclosure, the antigen-binding fragment may be selected from a group consisting of Fab fragment, Fab' fragment, F(ab')2 fragment, Fd fragment, Fd' fragment, Fv fragment, scFv fragment, ds-scFv fragment, dAb fragment, single chain fragment, diabody and linear antibody.

In one aspect, the present disclosure relates to a nucleic acid molecule, wherein the nucleic acid molecule comprises a nucleotide sequence encoding the antibody or antigen-binding fragment thereof of the present disclosure.

In another aspect, the present disclosure relates to a vector comprising a nucleic acid molecule of the present disclosure.

In yet another aspect, the present disclosure relates to a host cell comprising the nucleic acid molecule or vector of the present disclosure.

In one aspect, the present disclosure relates to a conjugate comprising any antibody or antigen-binding fragment thereof of the present disclosure conjugated to a therapeutic agent, a diagnostic agent or an imaging agent.

In another aspect, the present disclosure relates to a composition comprising the antibody or antigen-binding fragment thereof or the conjugate of the present disclosure, and one or more pharmaceutically acceptable carriers, excipients, and/or diluents. In some embodiments, the composition further comprises one or more additional therapeutic agents.

In some embodiments, the therapeutic agents may be selected from a group consisting of antibody, chemotherapeutic, and small molecule drug. In some embodiments, the chemotherapeutic may be selected from one or more of Epirubicin, Oxaliplatin, and 5-Fluorouracil (5-FU).

In one aspect, the present disclosure relates to a method of treating a disease associated with the expression of CLDN18.2 in a subject, the method comprises a step of administering to the subject the antibody or antigen-binding fragment thereof, or the conjugate, or the composition of the present disclosure.

In some embodiments, the disease is a cancer. For example, the cancer may be selected from a group consisting of gastric cancer, cholangiocarcinoma, esophageal cancer, and pancreatic cancer.

In some embodiments, the method further comprises a step of administering to the subject one or more additional therapies, for example, a cancer therapy. In some embodiments, the additional therapy is selected from a group consisting of chemotherapy, radiation therapy, immunotherapy, and surgery.

In some embodiments, the immunotherapy is selected from a group consisting of therapy targeting an immune checkpoint molecule, CAR-T cell therapy, and CAR-NK cell therapy.

In some embodiments, the chemotherapy is selected from a combined chemotherapy regimen comprising Epirubicin, Oxaliplatin, and 5-fluorouracil.

In one aspect, the present disclosure relates to use of the antibody or antigen-binding fragment thereof, the conjugate, or the composition of the present disclosure in treating a disease associated with the expression of CLDN18.2 in a subject.

In another aspect, the present disclosure relates to use of the antibody or antigen-binding fragment thereof, the conjugate, or the composition of the present disclosure in the manufacture of a medicament for treating a disease associated with the expression of CLDN18.2 in a subject.

In some embodiments of the uses in the present disclosure, the disease is a cancer. For example, the cancer may be selected from a group consisting of gastric cancer, cholangiocarcinoma, esophageal cancer, and pancreatic cancer.

In one aspect, the present disclosure relates to a polypeptide having an amino acid sequence selected from SEQ ID NOs: 1, 6, 11, 16, 21, 26, 31, 36, 41, 46, 55, and 60.

In another aspect, the present disclosure relates to a nucleic acid molecule having a nucleotide sequence selected from SEQ ID NOs: 2, 7, 12, 17, 22, 27, 32, 37, 42, 47, 56, and 61. The present disclosure also relates to a vector comprising above nucleic acid molecule.

DESCRIPTION OF THE DRAWINGS

FIG. 8A shows the fitted curves of the binding of the antibodies to FcγRIIIa, and FIG. 8B shows the Ka, Kd, KD and tc values of the binding of the antibodies to FcγRIIIa.

FIG. 9A shows the results of binding of the antibodies to FcγRIIIa-Jurkat cells. FIG. 9B shows the results of the binding of the antibodies to NK92MI cells.

DETAILED DESCRIPTION OF THE INVENTION

Figure 1:
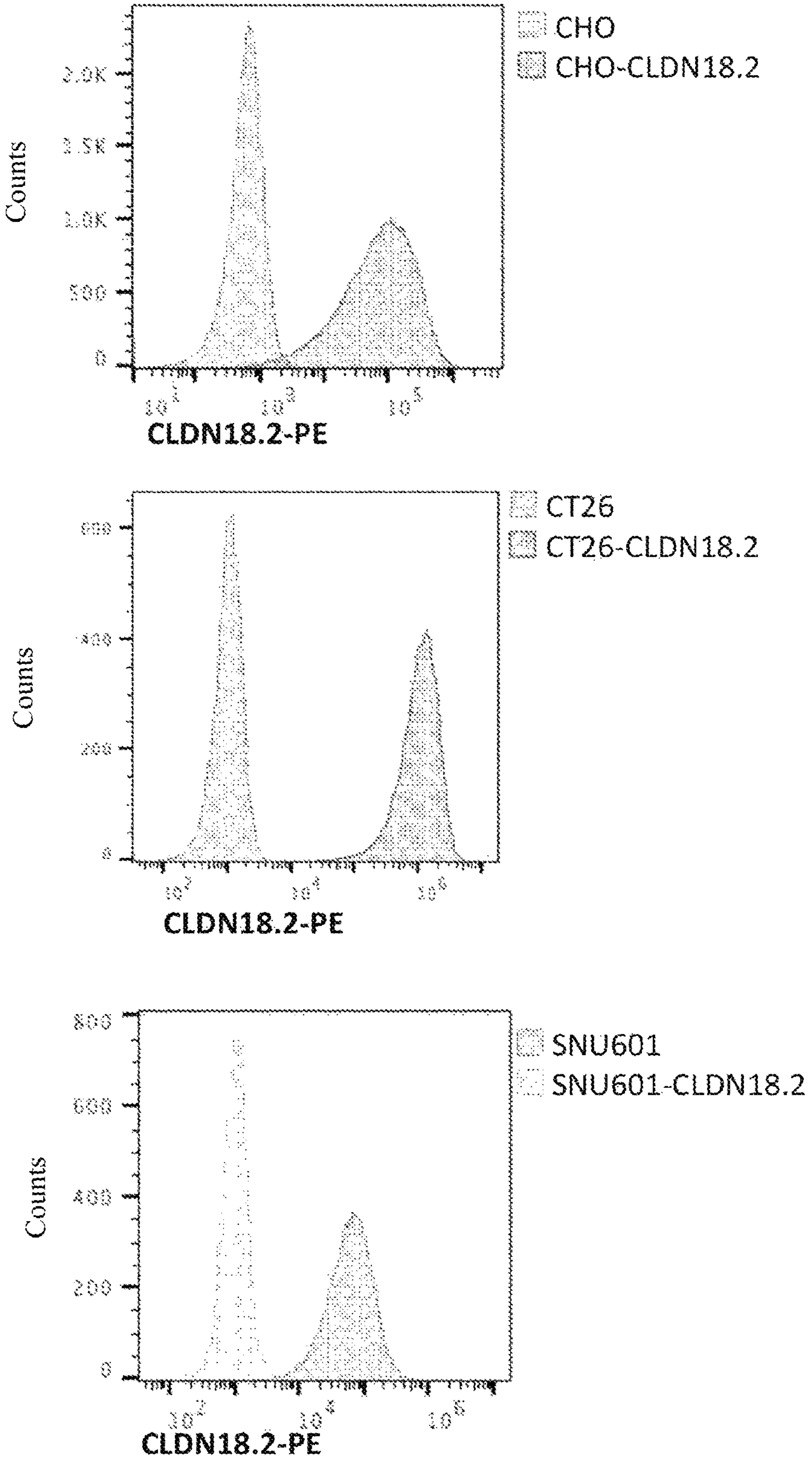
FIG. 1 shows the results of CLDN18.2 expression in CHO, CT26, SNU601 cells as well as the constructed CHO-CLDN18.2, CT26-CLDN18.2, and SNU601-CLDN18.2 cells, as tested by flow cytometry.

Unless otherwise defined herein, the scientific and technical terms and abbreviations thereof used in conjunction with the present invention shall have the meanings commonly understood by those of ordinary skill in the art to which the present invention belongs. Some of the terms and abbreviations used herein are listed below.

Antibody: Ab; immunoglobulin: Ig;
heavy chain: HC; light chain: LC;
heavy chain variable domain: VH;
heavy chain constant domain: CH;
light chain variable domain: VL;
light chain constant domain: CL;
complementary determining region: CDR;
Fab fragment: antigen-binding fragment, Fab;
Fc region: fragment crystallizable region, Fc;
monoclonal antibody: mAb;
antibody-dependent cell-mediated cytotoxicity: ADCC;
complement dependent cytotoxicity: CDC.

In one aspect, the present disclosure relates to an antibody that binds to CLDN18.2 or an antigen-binding fragment thereof, wherein the antibody has the following heavy chain CDRs (CDRHs) and light chain CDRs (CDRLs):

a. CDRH1, CDRH2 and CDRH3 in a heavy chain variable region (VH) as shown in SEQ ID NO: 1; and CDRL1, CDRL2 and CDRL3 in a light chain variable region (VL) as shown in SEQ ID NO: 6;
b. CDRH1, CDRH2 and CDRH3 in a VH as shown in SEQ ID NO: 11; and CDRL1, CDRL2 and CDRL3 in a VL as shown in SEQ ID NO: 16;
c. CDRH1, CDRH2 and CDRH3 in a VH as shown in SEQ ID NO: 21; and CDRL1, CDRL2 and CDRL3 in a VL as shown in SEQ ID NO: 26;
d. CDRH1, CDRH2 and CDRH3 in a VH as shown in SEQ ID NO: 31; and CDRL1, CDRL2 and CDRL3 in a VL as shown in SEQ ID NO: 36;
e. CDRH1, CDRH2 and CDRH3 in a VH as shown in SEQ ID NO: 41; and CDRL1, CDRL2 and CDRL3 in a VL as shown in SEQ ID NO: 46; or
f. CDRH1, CDRH2 and CDRH3 in a VH as shown in SEQ ID NO: 55; and CDRL1, CDRL2 and CDRL3 in a VL as shown in SEQ ID NO: 60.

As used herein, the term "binding" or "specific binding" refers to a non-random binding reaction between two molecules, such as the reaction between an antibody and the antigen against which it is directed. In certain embodiments, an antibody that specifically binds to a certain antigen (or an antibody specific to a certain antigen) refers to an antibody binding to the antigen with an affinity ($K_D$) of less than about $10^{-5}$M, for example less than about $10^{-6}$ M, $10^{-7}$M, $10^{-8}$M, $10^{-9}$M, or $10^{-10}$ M or less. As used herein, "$K_D$" refers to the dissociation equilibrium constant of a particular antibody-antigen interaction and is used to describe the binding affinity between an antibody and an antigen. The smaller the dissociation equilibrium constant, the tighter the antibody-antigen binding, and the higher the affinity between the antibody and the antigen.

As used herein, the term "antibody" refers to an immunoglobulin molecule that comprises at least one antigen recognition site and is able to specifically bind to an antigen. The term "antigen" refers to a substance, such as a protein, polypeptide, peptide, carbohydrate, polynucleotide, lipid, hapten, or a combination thereof, that induces an immune response in the body and binds specifically to an antibody. The binding of an antibody and an antigen is mediated by the interaction formed between the two, including hydrogen bond, van der Waals force, ionic bond, and hydrophobic bond. The region of an antigen surface to which an antibody binds is an "antigenic determinant" or "epitope", and in general, each antigen may have multiple epitopes.

As used herein, the term "epitope" may be formed by contiguous amino acids or non-contiguous amino acids that are brought together by the folding of a protein. An Epitope typically comprises at least 3, more often at least 5, about 9, or about 8-10 amino acids in a unique spatial conformation. An "epitope" includes a structural unit normally bound by an immunoglobulin VH/VL pair. An epitope defines the smallest binding site of an antibody and thus represents a target specific to an antibody or antigen-binding fragment thereof.

The term "antibody" as used in this disclosure is understood in its broadest meaning, and includes monoclonal antibodies (including full-length monoclonal antibodies), polyclonal antibodies, antibody fragments, multi-specific antibodies comprising at least two different antigen-binding structural domains (e.g., bispecific antibodies). Antibody also includes mouse-derived antibodies, humanized antibodies, chimeric antibodies, human antibodies, and antibodies from other sources. Antibody may contain additional alterations, such as unnatural amino acids, Fc effector function mutations, and glycosylation site mutations. Antibody may also include post-translationally modified antibodies, fusion proteins comprising the antigenic determinant cluster of antibodies, and immunoglobulin molecules comprising any other modifications to the antigen recognition site, provided that these antibodies exhibit the desired biological activity. In other words, include immunoglobulin molecules and immunologically active fragments of immunoglobulin molecules, i.e., molecules that contain at least one antigen-binding domain.

As used herein, "variable region" (heavy chain variable region VH and light chain variable region VL) refers to paired light and heavy chain domain portions that directly participate in the binding of an antibody and an antigen. Each VH and VL region consists of three highly variable regions or complementary determining regions (CDRs) and four framework regions (FRs) arranged from N-terminal to C-terminal in the following order: FR1, CDR1, FR2, CDR2, FR3, CDR3, FR4.

As used herein, the term "CDR" refers to the complementary determining region within the variable sequence of an antibody. For each variable region, there are three CDRs in each variable region of the heavy chain and light chain, which are called CDR1, CDR2, and CDR3. The exact boundaries of these CDRs are defined differently according to different systems. The system described by Kabat et al. (Kabat et al., Sequences of Proteins of Immunological Interest (National Institutes of Health, Bethesda, Md. (1987) and (1991)) provides not only an explicit residue numbering system applicable to antibody variable regions, but also residue boundaries that define three CDRs. These CDRs may be called Kabat CDRs. Each complementary determining region can comprise the amino acid residues of the "complementary determining region" defined by Kabat. Chothia et al. (Chothia & Lesk, J. Mol. Biol, 196:901-917 (1987) and Chothia et al., Nature 342:877-883 (1989)) found that certain subparts within the Kabat CDRs adopt an almost identical peptide backbone conformation, despite the diversity at the amino acid sequence level. These subparts are called L1, L2 and L3 or H1, H2 and H3, respectively, where "L" and "H" denote the light and heavy chain regions, respectively. These regions can be called Chothia CDRs, which have overlapping boundaries with Kabat CDRs. There are other CDR boundary definitions that may not strictly follow one of the above systems, but will still overlap with the Kabat CDRs. The method used herein may utilize CDRs defined according to any of these systems, although a preferred embodiment uses the CDRs defined by Kabat or Chothia.

When the Kabat system is used to define CDR sequences, the CDRH1, CDRH2, and CDRH3 in a VH as shown in SEQ ID NO: 1 have amino acid sequences of SEQ ID NO: 3 (SSWLI), SEQ ID NO: 4 (TIVPSDSYTNYNQKFKD) and SEQ ID NO: 5 (FRTGNSFDY), respectively, and the CDRL1, CDRL2, and CDRL3 in a VL as shown in SEQ ID NO: 6 have amino acid sequences of SEQ ID NO: 8 (KSSQSVLNSGNQKNYLT), SEQ ID NO: 9 (WAVARQS) and SEQ ID NO: 10 (QNSIAYPFT), respectively;

the CDRH1, CDRH2 and CDRH3 in a VH as shown in SEQ ID NO: 11 have the amino acid sequences of SEQ ID NO: 13 (SFWVG), SEQ ID NO: 14 (NVSPSDSYTNYNQKFKD) and SEQ ID NO: 15 (LSSGNSFDY), respectively, and the CDRL1, CDRL2 and CDRL3 in a VL as shown in SEQ ID NO: 16 have the amino acid sequences of SEQ ID NO: 18 (KSSQSVLNSGNQKNYLT), SEQ ID NO: 19 (WSSTKQS) and SEQ ID NO: 20 (QNAFSFPFT), respectively;

the CDRH1, CDRH2 and CDRH3 in a VH as shown in SEQ ID NO: 21 have the amino acid sequences of SEQ ID NO: 23 (SYWLN), SEQ ID NO: 24 (SMYPSDSYTNYNQKFKD) and SEQ ID NO: 25 (FSRGNSFDY), respectively, and the CDRL1, CDRL2 and CDRL3 in a VL as shown in SEQ ID NO: 26 have the amino acid sequences of SEQ ID NO: 28 (KSSQSLLESGNQKNYLT), SEQ ID NO: 29 (WSWAKNS) and SEQ ID NO: 30 (QNAYAFPFT), respectively;

the CDRH1, CDRH2 and CDRH3 in a VH as shown in SEQ ID NO: 31 have the amino acid sequences of SEQ ID NO: 33 (SFWIS), SEQ ID NO: 34 (NILPSDSYTNYNQKFKD) and SEQ ID NO: 35 (YWRGNSFDY), respectively, and the CDRL1, CDRL2 and CDRL3 in a VL as shown in SEQ ID NO: 36 have the amino acid sequences of SEQ ID NO: 38

(KSSQSIINSGNQKNYLT), SEQ ID NO: 39 (WGGTRHS) and SEQ ID NO: 40 (QNGYYSPFT), respectively;

the CDRH1, CDRH2 and CDRH3 in a VH as shown in SEQ ID NO: 41 have the amino acid sequences of SEQ ID NO: 43 (SSWVG), SEQ ID NO: 44 (NSYPSD-SYTNYNQKFKD) and SEQ ID NO: 45 (LGRGNSFDY), respectively, and the CDRL1, CDRL2 and CDRL3 in a VL as shown in SEQ ID NO: 46 have the amino acid sequences of SEQ ID NO: 48 (KSSQSLIHSGNQKNYLT), SEQ ID NO: 49 (WGL-SKNS) and SEQ ID NO: 50 (QNSIYYPFT), respectively;

the CDRH1, CDRH2 and CDRH3 in a VH as shown in SEQ ID NO: 55 have the amino acid sequences of SEQ ID NO: 57 (SYWLG), SEQ ID NO: 58 (IIYPSD-SYTNYNQKFKD) and SEQ ID NO: 59 (FWRGNSFDY), respectively, and the CDRL1, CDRL2 and CDRL3 in a VL as shown in SEQ ID NO: 60 have the amino acid sequences of SEQ ID NO: 62 (KSSQSLLESGNQKNYLT), SEQ ID NO: 63 (WAAGKES) and SEQ ID NO: 64 (QNGYSHPFT), respectively.

Accordingly, in some embodiments of the antibody or antigen-binding fragment thereof of the present disclosure, the antibody has the following CDRHs and CDRLs:

a. CDRH1, CDRH2 and CDRH3 as shown in SEQ ID NOs: 3-5; and CDRL1, CDRL2 and CDRL3 as shown in SEQ ID NOs: 8-10;
b. CDRH1, CDRH2 and CDRH3 as shown in SEQ ID NOs: 13-15; and CDRL1, CDRL2 and CDRL3 as shown in SEQ ID NOs: 18-20;
c. CDRH1, CDRH2 and CDRH3 as shown in SEQ ID NOs: 23-25; and CDRL1, CDRL2 and CDRL3 as shown in SEQ ID NOs: 28-30;
d. CDRH1, CDRH2 and CDRH3 as shown in SEQ ID NOs: 33-35; and CDRL1, CDRL2 and CDRL3 as shown in SEQ ID NOs: 38-40;
e. CDRH1, CDRH2 and CDRH3 as shown in SEQ ID NOs: 43-45; and CDRL1, CDRL2 and CDRL3 as shown in SEQ ID NOs: 48-50;
f. CDRH1, CDRH2 and CDRH3 as shown in SEQ ID NOs: 57-59; and CDRL1, CDRL2 and CDRL3 as shown in SEQ ID NOs: 62-64.

In some embodiments of the antibody or antigen-binding fragment thereof of the present disclosure, the antibody has the following VH and VL:

a. VH comprising the amino acid sequence of SEQ ID NO: 1, and VL comprising the amino acid sequence of SEQ ID NO: 6;
b. VH comprising the amino acid sequence of SEQ ID NO: 11, and VL comprising the amino acid sequence of SEQ ID NO: 16;
c. VH comprising the amino acid sequence of SEQ ID NO: 21, and VL comprising the amino acid sequence of SEQ ID NO: 26;
d. VH comprising the amino acid sequence of SEQ ID NO: 31, and VL comprising the amino acid sequence of SEQ ID NO: 36;
e. VH comprising the amino acid sequence of SEQ ID NO: 41, and VL comprising the amino acid sequence of SEQ ID NO: 46; or
f. VH comprising the amino acid sequence of SEQ ID NO: 55, and VL comprising the amino acid sequence of SEQ ID NO: 60.

In some other embodiments of the antibody or antigen-binding fragment thereof of the present disclosure, the antibody has the following VH and VL:

a. VH comprising the amino acid sequence of SEQ ID NO: 1 with one or more amino acid modifications, and VL comprising the amino acid sequence of SEQ ID NO: 6 with one or more amino acid modifications;
b. VH comprising the amino acid sequence of SEQ ID NO: 11 with one or more amino acid modifications, and VL comprising the amino acid sequence of SEQ ID NO: 16 with one or more amino acid modifications;
c. VH comprising the amino acid sequence of SEQ ID NO: 21 with one or more amino acid modifications, and VL comprising the amino acid sequence of SEQ ID NO: 26 with one or more amino acid modifications;
d. VH comprising the amino acid sequence of SEQ ID NO: 31 with one or more amino acid modifications, and VL comprising the amino acid sequence of SEQ ID NO: 36 with one or more amino acid modifications;
e. VH comprising the amino acid sequence of SEQ ID NO: 41 with one or more amino acid modifications, and VL comprising the amino acid sequence of SEQ ID NO: 46 with one or more amino acid modifications; or
f. VH comprising the amino acid sequence of SEQ ID NO: 55 with one or more amino acid modifications, and VL comprising the amino acid sequence of SEQ ID NO: 60 with one or more amino acid modifications.

In some embodiments, the amino acid modification does not change the CDR sequences of the antibody, i.e., the amino acid modification is performed in a framework region (FR) of a variable region.

In some embodiments, the one or more amino acid modifications refer to 1-10 amino acid modifications or 1-5 amino acid modifications, for example 1, 2, 3, 4, 5, 6, 7, 8, 9 or 10 amino acid modifications.

In some embodiments, the amino acid modifications are selected from substitution, deletion, addition and/or insertion of amino acid residues. In some embodiments, said amino acid modifications are amino acid substitutions, for example conservative substitutions.

In some embodiments of the antibody or antigen-binding fragment thereof of the present disclosure, the antibody has the following VH and VL:

a. VH comprising an amino acid sequence having at least 80% sequence identity, for example at least 90%, at least 95%, at least 98%, or at least 99% sequence identity, with the amino acid sequence of SEQ ID NO: 1, and VL comprising an amino acid sequence having at least 80% sequence identity, for example at least 90%, at least 95%, at least 98%, or at least 99% sequence identity, with the amino acid sequence of SEQ ID NO: 6;
b. VH comprising an amino acid sequence having at least 80% sequence identity, for example at least 90%, at least 95%, at least 98%, or at least 99% sequence identity, with the amino acid sequence of SEQ ID NO: 11, and VL comprising an amino acid sequence having at least 80% sequence identity, for example at least 90%, at least 95%, at least 98%, or at least 99% sequence identity, with the amino acid sequence of SEQ ID NO: 16
c. VH comprising an amino acid sequence having at least 80% sequence identity, for example at least 90%, at least 95%, at least 98%, or at least 99% sequence identity, with the amino acid sequence of SEQ ID NO: 21, and VL having an amino acid sequence sharing at least 80% sequence identity, for example at least 90%, at least 95%, at least 98%, or at least 99% sequence identity, with the amino acid sequence of SEQ ID NO: 26;

d. VH comprising an amino acid sequence having at least 80% sequence identity, for example at least 90%, at least 95%, at least 98%, or at least 99% sequence identity, with the amino acid sequence of SEQ ID NO: 31, and VL comprising an amino acid sequence having at least 80% sequence identity, for example at least 90%, at least 95%, at least 98%, or at least 99% sequence identity, with the amino acid sequence of SEQ ID NO: 36 e. VH comprising an amino acid sequence having at least 80% sequence identity, for example at least 90%, at least 95%, at least 98%, or at least 99% sequence identity, with the amino acid sequence of SEQ ID NO: 41, and VL comprising an amino acid sequence having at least 80% sequence identity, for example at least 90%, at least 95%, at least 98%, or at least 99% sequence identity, with the amino acid sequence of SEQ ID NO: 46; or f. VH comprising an amino acid sequence having at least 80% sequence identity, for example at least 90%, at least 95%, at least 98%, or at least 99% sequence identity, with the amino acid sequence of SEQ ID NO: 55, and VL comprising an amino acid sequence having at least 80% sequence identity, for example at least 90%, at least 95%, at least 98%, or at least 99% sequence identity, with the amino acid sequence of SEQ ID NO: 60.

As understood by those skilled in the art, the correlation between two amino acid sequences or between two nucleotide sequences can be described by the parameter "sequence identity". The percentage of sequence identity between two sequences can be determined, for example, by using a mathematical algorithm. The percentage of sequence identity between two sequences can be determined, for example, by using a mathematical algorithm. Non-limiting examples of such mathematical algorithms include the algorithm of Myers and Miller (1988) CABIOS 4:11-17, the local homology algorithm of Smith et al., (1981) Adv. Appl. Math. 2:482, the homology comparison algorithm of Needleman and Wunsch (1970) J. Mol. Biol. 48:443-453, the method for searching for homology of Pearson and Lipman (1988) Proc. Natl. Acad. Sci. 85:2444-2448, and the modified algorithm of Karlin and Altschul (1990) Proc. Natl. Acad. Sci. USA 87:2264, which is described in Karlin and Altschul (1993) Proc. Natl. Acad. Sci. USA 90:5873-5877. By using programs based on such mathematical algorithms, sequence comparisons (i.e., alignments) for determining sequence identity can be implemented. The programs can be properly executed by a computer. Examples of such programs include, but are not limited to, CLUSTAL of the PC/Gene program, the ALIGN program (Version 2.0), and GAP, BESTFIT, BLAST, FASTA, and TFASTA in the Wisconsin Genetics software package. The alignment using these programs can be implemented, for example, by using initial parameters.

In some embodiments of the antibody or antigen-binding fragment thereof of the present disclosure, the antibody may have a heavy chain constant region sequence as shown in SEQ ID NO: 51 and/or a light chain constant region sequence as shown in SEQ ID NO: 53.

In some embodiments of the antibody or antigen-binding fragment thereof of the present disclosure, the antibody has an Fc region. In some embodiments, the antibody has a glycosyl structure modification at Asn297, wherein the numbering is according to the Eu numbering system. "Asn297" according to the present disclosure means asparagine located at position 297 in the Fc region of an antibody according to the Eu numbering system. Asn297 may also be located a few amino acids upstream or downstream of position 297 based on subtle sequence changes of the specific antibody.

As used herein, the term "Fc region of an antibody" or "human immunoglobulin Fc region" comprises the constant region polypeptide of an antibody other than the heavy chain constant region 1 (CH1), for example, two constant region domains (CH2 and CH3) at the carboxyl terminus of the heavy chain constant regions of human immunoglobulins IgA, IgD, IgG, and three constant region domains (CH2, CH3 and CH4) at the carboxyl terminus of the heavy chain constant regions of human immunoglobulins IgE and IgM, and also includes the flexible hinge regions at the amino terminus of these domains. Although the boundaries of the Fc region can vary, the heavy chain Fc region of human IgG is typically defined as comprising the residues starting from A231 to its carboxy terminus.

The Fc region of immunoglobulin is the functional domain which exerts the immune effect of an antibody. The Fc of an IgG antibody can interact with a variety of receptors, the most important of which is the Fcγ receptor (FcγR) family. A major mechanism of action of therapeutic monoclonal antibodies to kill tumor cells is the ADCC effect (antibody dependent cell mediated cytotoxicity). Upon binding of the antigen recognition region of a therapeutic antibody to a specific antigen on the surface of tumor cells, the Fc region of the antibody binds to killer cells expressing FcγR and activate the cell killing activity of the effector cells, thus secreting cytotoxic mediators including granzymes, perforins, etc., which ultimately lead to the lysis and destruction of target cells (e.g. tumor cells). In addition, Fc can also bind to the complement protein C1q and produce a CDC effect (complement dependent cytotoxicity, CDC).

The level and form of glycosylation modification in the Fc region of an antibody can affect the binding ability of the Fc region to its receptor FcγR, thereby affecting the strength of the ADCC effect of the antibody. As used herein, the glycosylation modification of the Fc region of an antibody usually refers to the glycosylation modification at Asn297. During the production of an antibody, it undergoes glycosylation in the ER and in the Golgi network of cells. In researches for antibody glycosylation, it is found that reducing the level of fucosylation of the antibody facilitates the increased binding of the Fc region to FcγRIIIa, thereby enhancing the ADCC effect of the antibody. Thus, altering the metabolic pathway of glycosylation in antibody-expressing cells can effectively alter the level of fucosylation in expressed antibodies, thereby modulating the antibody-mediated ADCC effect (Jefferis R. 2009, NAT. REV. Drug. DISC).

Accordingly, in some embodiments of the antibody or antigen-binding fragment thereof of the present disclosure, the antibody has a reduced level of fucosylation. For example, in some embodiments of the antibody or antigen-binding fragment thereof of the present disclosure, the ratio of the glycosyl structure having fucose in the glycosyl structure at Asn297 is 60% or less, e.g., 50% or less, e.g., 40% or less, 30% or less, 20% or less, 10% or less, 5% or less, 2% or less, or 1% or less. In some embodiments, the ratio of the glycosyl structure having fucose is 0%-10%, e.g., 0%-5%, 0%-2%, or 0%-1%. In some embodiments, the ratio of the glycosyl structure having fucose is 0.1% or less. In other embodiments, there is no detectable fucose in the glycosyl structure at Asn297.

Such defucosylated antibodies can be generated using techniques known to those skilled in the art. For example, the antibodies can be expressed in cells that are defective of or lack of the ability to fucosylation. In some embodiments, for example, cell lines with Fut8 gene knockout can be used to produce antibodies with reduced levels of fucosylation. Alternatively, antibody or antigen-binding fragment having reduced or no fucose content can be produced by, for example: (i) culturing cells under conditions that prevent or reduce fucosylation; (ii) removing fucose after translation (e.g., with fucosidase); (iii) adding desired carbohydrates after translation, e.g., after recombinant expression of non-glycosylated glycoproteins; or (iv) purifying glycoproteins to select for the antibody or antigen-binding fragment thereof that is not fucosylated.

In some embodiments of the antibody or antigen-binding fragment thereof of the present disclosure, the antibody is produced by a cell with Fut8 gene knockout to obtain the antibody with reduced level of fucosylation. In some embodiments, the cell is Chinese Hamster Ovary (CHO) cell, such as CHO-K1 cell, CHOS cell, or other CHO-derived cells. In some embodiments, the cell is CHO cell with Fut8 gene knockout.

In some other embodiments, the cell is human embryonic kidney (HEK) 293 cell, such as HEK293, HEK293A, HEK293T, HEK293F, or other HEK293-derived cells. In some embodiments, the cell is HEK 293 cell with Fut8 gene knockout.

In some embodiments of the antibody or antigen-binding fragment thereof of the present disclosure, the antibody is produced by a cell with Fut8 gene knockout, wherein the antibody has an increased FcγRIIIa binding activity, as compared to an antibody produced in a cell without Fut8 gene knockout, e.g., a control antibody with the identical sequence. In some embodiments, an antibody produced by a cell with Fut8 gene knockout has an increased ability to induce FcγRIIIa activity as compared to an antibody produced in a cell without Fut8 gene knockout, e.g., a control antibody with the identical sequence. For example, in some embodiments, an antibody produced by a cell with Fut8 gene knockout has at least 2-fold, e.g., at least 5-fold or at least 10-fold, e.g., 10 to 20-fold, increased EC50 values for inducing FcγRIIIa activity, as compared to an antibody produced in a cell without Fut8 gene knockout. As used herein, the term "EC50" refers to the concentration of an antibody inducing 50% of the maximum effect.

In some embodiments of the antibody or antigen-binding fragment thereof of the present disclosure, the antibody is produced by a cell with Fut8 gene knockout, and wherein the antibody has an increased ADCC activity, as compared to an antibody produced in a cell without Fut8 gene knockout, e.g., a control antibody with the identical sequence. For example, in some embodiments, an antibody produced by a cell with Fut8 gene knockout has at least 2-fold, e.g., at least 5-fold or at least 10-fold, e.g., 10 to 20-fold increased ADCC activity, as compared to an antibody produced in a cell without Fut8 gene knockout.

In some embodiments of the antibody or antigen-binding fragment thereof of the present disclosure, the antibody is a monoclonal antibody.

As used herein, the term "monoclonal antibody" refers to an antibody obtained from a substantially homogeneous antibody population, i.e., each antibody constituting the population is identical, except for possible naturally occurring mutations that may exist in small amounts. A monoclonal antibody is highly specific and is directed against a single antigen. Furthermore, in contrast to a polyclonal antibody preparation which typically include different antibodies directed against different determinants (epitopes), each antibody in a monoclonal preparation is directed against the same single determinant on an antigen. As used herein, the term "monoclonal antibody" is not limited to an antibody produced by hybridoma technology, and the modifier "monoclonal antibody" should not be interpreted as requiring the production of an antibody by any particular method.

In some embodiments of the antibody or antigen-binding fragment thereof of the present disclosure, the antibody is a bispecific antibody or a multispecific antibody.

For example, the bispecific or multispecific antibody has a first antigen-binding region that binds to an epitope on CLDN 18.2, and a second antigen-binding region that binds to another antigenic epitope, wherein the first antigen-binding region has the CDRH1, CDRH2 and CDRH3 as well as CDRL1, CDRL2 and CDRL3, or VH and VL sequences of the antibody or antigen-binding fragment thereof as described in the present disclosure, and the second antigen-binding region binds to a different antigenic epitope than the first antigen-binding region.

In some embodiments, the second antigen-binding region binds to another antigen-binding epitope on the CLDN18.2 molecule. In other embodiments, the second antigen-binding region binds to another antigen. In some embodiments, said another antigen is selected from tumor-associated antigens and immune checkpoint molecules.

Many tumor-associated antigens associated with specific cancers have been identified in the field. As used herein, the term "tumor-associated antigen" refers to antigen that is differentially expressed by cancer cells and therefore can be utilized to target cancer cells. Tumor-associated antigen is an antigen that can potentially stimulate a significant tumor-specific immune response. Some of these antigens are encoded by normal cells, but not necessarily expressed by normal cells. These antigens can be characterized as those that are usually silent (i.e., not expressed) in normal cells, those that are expressed only at certain stages of differentiation, and those that are expressed over time, such as embryonic and fetal antigens. Other cancer antigens are encoded by mutant cytogenes such as oncogenes (e.g., activated ras oncogenes), suppressor genes (e.g., mutant p53), and fusion proteins produced by internal deletions or chromosomal translocations. Other cancer antigens can be encoded by viral genes, such as those carried on RNA and DNA tumor viruses. Many other tumor-associated antigens and antibodies against them are known and/or commercialized, and can also be generated by those skilled in the art.

Immune checkpoint protein receptors and their ligands (collectively referred to herein as immune checkpoint molecules) mediate the suppression of T cell-mediated cytotoxicity, and are typically expressed by tumors or on nonreactive T cells in the tumor microenvironment, and allow tumors to evade immune attack. Inhibitors of the activity of immunosuppressive checkpoint protein receptors and their ligands can overcome the immunosuppressive tumor environment to allow cytotoxic T-cell attack of tumors. Examples of immune checkpoint proteins include, but are not limited to, PD-1, PD-L1, PD-L2, CTLA4, OX40, LAG3, TIM3, TIGIT, and CD103. Regulation (including inhibition) of the activity of such proteins can be accomplished by immune checkpoint modulators, which can include, for example, antibodies targeting checkpoint proteins, aptamers, small molecules, and soluble forms of checkpoint receptor proteins. Antibodies specific for PD-1, PD-L2, CTLA4, OX40, LAG3, TIM3, TIGIT, and CD103 are known and/or commerciallized, and can also be generated by those skilled in the art.

According to the amino acid sequence of heavy chain constant region of an antibody, immunoglobulins can be divided into 5 classes (isotypes): IgA, IgD, IgE, IgG and IgM, which can be further divided into different subclasses, such as IgG1, IgG2, IgG3, IgG4, IgA1, IgA2, etc. According to the amino acid sequence of light chain, light chains can be classified as λ chain or κ chain. The antibody of the present disclosure can be any of the above-mentioned classes or subclasses.

In some embodiments, the antibody of the present disclosure is selected from a group consisting of IgG, IgA, IgM, IgE, and IgD isotypes. In some embodiments, the antibody of the present disclosure is IgG, for example selected from a group consisting of IgG1, IgG2, IgG3, and IgG4 subclasses.

As used herein, the term "antigen-binding fragment" includes, but is not limited to: Fab fragment having VL, CL, VH and CH1 domains; Fab' fragment, which is a Fab fragment with one or more cysteine residues at the C-terminus of the CH1 domain; Fd fragment, which has VH and CH1 domains; Fd' fragment, which has VH and CH1 domains and one or more cysteine residues at the C-terminus of the CH1 domain; Fv fragment and scFv, which have the VL and VH domains of a single arm of an antibody; dAb fragment, which consists of either a VH or VL domain; isolated CDR region; F(ab')2 fragment, which is a bivalent fragment comprising two Fab' fragments linked by a disulfide bridge at the hinge region; single-chain antibody molecule (e.g., single chain Fv; scFv); "diabody" having two antigen binding sites, which comprises a heavy chain variable domain (VH) linked to a light chain variable domain (VL) in the same polypeptide chain; "linear antibody" comprising a pair of tandem Fd segments (VH-CH1-VH-CH1) that together with a complementary light chain polypeptide forms a pair of antigen binding regions; and a modified form of any of the preceding substances, which retains antigen binding activity.

In some embodiments of the antibody or antigen-binding fragment thereof of the present disclosure, the antigen-binding fragment is selected from a group consisting of Fab fragment, Fab' fragment, $F(ab')_2$ fragment, Fd fragment, Fd' fragment, Fv fragment, scFv fragment, ds-scFv fragment, dAb fragment, single chain fragment, diabody and linear antibody.

In another aspect, the present disclosure relates to a nucleic acid molecule comprising a nucleotide sequence encoding the antibody or antigen-binding fragment thereof of the present disclosure. The present disclosure also relates to a vector comprising the nucleic acid molecule of the present disclosure.

As used herein, "vector" refers to a nucleic acid delivery vehicle into which a polynucleotide can be inserted. When the vector enables the expression of the proteins encoded by the inserted polynucleotide, the vector is called an expression vector. The vector can be introduced into a host cell by methods such as transformation, transduction, or transfection, and subsequently a genetic material element it carries can be expressed in the host cell. The vector is recognized by those skilled in the art, including but not limited to, (1) plasmids; (2) phage particles; (3) Coase plasmids; (4) artificial chromosomes, such as yeast artificial chromosomes, bacterial artificial chromosomes or P1-derived artificial chromosomes; (5) phages such as λ phages or M13 phages and (6) animal viruses, such as retroviruses, adenoviruses, adeno-associated viruses, sporoviruses, poxviruses, and baculoviruses. A vector may contain a variety of elements that control expression, including, but not limited to, promoter sequences, transcription start sequences, enhancer sequences, selection elements, and reporter genes; in addition, the vector may contain replication initiation sites.

In one aspect, the present disclosure relates to a host cell comprising the nucleic acid molecule or vector of the present disclosure. In some embodiments, the host cell is CHO cell, e.g., CHO-K1 cell, CHOS cell, or other CHO-derived cells. In other embodiments, the host cell is HEK 293 cell, for example HEK293, HEK293A, HEK293T, HEK293F, or other HEK293-derived cell.

In one aspect, the present disclosure relates to a conjugate comprising the antibody or antigen-binding portion thereof of the present disclosure conjugated to a therapeutic agent, a diagnostic agent, or an imaging agent. In some embodiments, the therapeutic agent may be selected from cytotoxins and radioisotopes. In some embodiments, the diagnostic agent or imaging agent may be selected from a group consisting of fluorescent markers, luminescent substances, chromogenic substances, and enzymes.

In another aspect, the present disclosure relates to a composition comprising the antibody or antigen-binding fragment thereof or the conjugate of the present disclosure, and one or more pharmaceutically acceptable carriers, excipients, and/or diluents.

The phrase "pharmaceutically acceptable" refers to those compounds, materials, compositions, and/or dosage forms that are suitable for use in contact with human and animal tissues without excessive toxicity, irritation, allergic response, or other problems or complications, within the scope of reasonable medical judgment, commensurate with a reasonable benefit/risk ratio. As used herein, the phrase "pharmaceutically acceptable carriers, excipients and/or diluents" refers to pharmaceutically acceptable materials, compositions or vehicles, such as liquid or solid fillers, diluents, excipients, solvents, medium, encapsulating materials, manufacturing aids or solvent encapsulating materials, which are involved in maintaining the stability, solubility, or activity of the antibody or antigen-binding fragment thereof of the present disclosure.

The composition of the present disclosure can be formulated for administration to a subject in a solid, liquid, or gel form. For example, the composition of the present disclosure can be formulated for parenteral administration, e.g., by subcutaneous, intramuscular, intravenous or epidural injection, as, e.g., a sterile solution or suspension or a sustained release formulation.

In some embodiments, the composition further comprises one or more additional therapeutic agents. In some embodiments, the additional therapeutic agent is selected from a group consisting of antibody, chemotherapeutic, and small molecule drug. In some embodiments, the therapeutic agent targets a tumor-associated antigen, e.g., a tumor-associated antigen as described above. In other embodiments, the therapeutic agent targets an immune checkpoint molecule, e.g., an immune checkpoint molecule as described above.

As used herein, the term "chemotherapeutic" refers to any chemical agent that has therapeutic usefulness in the treatment of diseases characterized by abnormal cell growth. The chemotherapeutic, as used herein, includes both chemical and biological agents. These agents function to inhibit the cellular activity upon which cancer cells depend to achieve sustained survival. The categories of chemotherapeutic agents include alkylating/alkaloid agents, antimetabolites, hormones or hormone analogs, and various anti-neoplastic drugs.

In some embodiments, the additional therapeutic agent is a chemotherapeutic, wherein the chemotherapeutic may be selected from one or more of Epirubicin, Oxaliplatin, and 5-fluorouracil (5-FU).

In one aspect, the present disclosure relates to a method of treating a disease associated with the expression of CLDN18.2 in a subject, comprising a step of administering to the subject the antibody or antigen-binding fragment thereof, conjugate or composition of the present disclosure.

As used herein, the term "treatment" refers to a therapeutic treatment in which the purpose is to reverse, reduce, improve, inhibit, slow down, or stop the progression or severity of a symptom associated with a disease or condition. The term "treatment" includes reducing or alleviating at least one side effect or symptom of a disease or condition. A treatment is generally "effective" if it reduces one or more symptoms or clinical markers. Alternatively, a treatment is "effective" if the progression of a disease is reduced or stopped, that is, the "treatment" includes not only an improvement in a symptom but also a cessation, or at least slowing down of the progression or worsening of a symptom that would be expected in the absence of treatment. Beneficial or desired clinical outcomes include, but are not limited to, alleviation of one or more symptoms, reduction in the extent of a disease, stabilization (i.e., no worsening) of a disease state, delay or slowing down of disease progression, improvement or alleviation of a disease state, and remission (whether partial or all), whether detectable or undetectable.

As used herein, the terms "subject", "patient", and "individual" are used interchangeably herein, and refer to an animal, e.g., a human. The term subject also includes "non-human mammal", for example, rat, mouse, rabbit, sheep, cat, dog, cattle, pig, and non-human primate. In a preferred embodiment, the subject is a human subject.

In some embodiments of the method described above, the disease is a cancer. Specific examples of the cancer include, but are not limited to: basal cell carcinoma, cholangiocarcinoma; bladder cancer; bone cancer; breast cancer; peritoneal cancer; cervical cancer; bile duct cancer; choriocarcinoma; colon and rectal cancer; connective tissue cancer; digestive system cancer; endometrial cancer; esophageal cancer; eye cancer; head and neck cancer; stomach cancer; glioblastoma; liver cancer; kidney cancer; laryngeal cancer; leukemia; liver cancer; lung cancer (e.g., small cell lung cancer, non-small cell lung cancer, lung adenocarcinoma, and squamous cell lung cancer); lymphoma, including Hodgkin's lymphoma and non-Hodgkin's lymphoma; melanoma; myeloma; neuroblastoma; oral cancer; ovarian cancer; pancreatic cancer; prostate cancer; retinoblastoma; rhabdomyosarcoma; rectal cancer; respiratory cancer; salivary gland cancer; sarcoma; skin cancer; squamous cell carcinoma; testicular cancer; thyroid cancer; cancer of the uterus or endometrium; urologic cancer; B-cell lymphoma; chronic lymphocytic leukemia (CLL); acute lymphoblastic leukemia (ALL); hairy cell leukemia; chronic myeloid leukemia; and the like. In a preferred embodiment, the cancer is selected from a group consisting of gastric cancer, cholangiocarcinoma, esophageal cancer, and pancreatic cancer.

In some embodiments of the method described above, the method further comprises a step of administering one or more additional therapies. For example, in some embodiments, the therapy is selected from a group consisting of chemotherapy, radiotherapy, immunotherapy, and surgical therapy.

In some embodiments, the immunotherapy is selected from a group consisting of a therapy targeting an immune checkpoint molecule, a CAR-T cell therapy, and a CAR-NK cell therapy. For example, the immune checkpoint molecule may be selected from a group consisting of PD-1, PD-L1, PD-L2, CTLA4, OX40, LAGS, TIM3, TIGIT, and CD103.

In some embodiments, the chemotherapy is selected from a combined chemotherapy regimen including Epirubicin, Oxaliplatin, and 5-fluorouracil.

In one aspect, the present disclosure relates to use of the antibody or antigen-binding fragment thereof, the conjugate, or the composition of the present disclosure in treating a disease associated with the expression of CLDN18.2 in a subject. In another aspect, the present disclosure relates to use of the antibody or antigen-binding fragment thereof, the conjugate, or the composition of the present disclosure in the manufacture of a medicament for treating a disease associated with the expression of CLDN18.2 in a subject.

In some embodiments of the uses described above, the disease is a cancer, for example, the cancer types described above. In a preferred embodiment, the cancer is selected from a group consisting of gastric cancer, cholangiocarcinoma, esophageal cancer, and pancreatic cancer.

In some embodiments of the uses described above, the subject is a human.

In one aspect, the present disclosure relates to a polypeptide having an amino acid sequence selected from SEQ ID NOs: 1, 6, 11, 16, 21, 26, 31, 36, 41, 46, 55, and 60.

In another aspect, the present disclosure relates to a nucleic acid molecule having a nucleotide sequence selected from SEQ ID NOs: 2, 7, 12, 17, 22, 27, 32, 37, 42, 47, 56, and 61. The present disclosure also relates to a vector comprising above-mentioned nucleic acid molecule.

EXAMPLES

The invention is further described below in conjunction with specific examples, the advantages and features of the invention will become clearer with the description. These examples, however, are only exemplary and do not constitute any limitation on the scope of the present invention. It should be understood by those skilled in the art that modifications or substitutions may be made to the details and forms of the technical solutions of the present invention without departing from the spirit and scope of the present invention, but such modifications and substitutions fall within the scope of protection of the present invention.

Example 1. Construction of Natural Phage Libraries

The development of antibody drugs is currently mainly achieved by humanizing antibodies derived from other species or directly screening fully human antibodies through transgenic animals and in vitro screening techniques, which further reduces the immunogenicity of antibodies in humans, reduces the corresponding side effects, and improves drugability, which is an important trend in antibody drug development.

Among the in vitro screening techniques, phage display antibody library technology is one of the main methods to obtain fully human antibodies. Phage display technology uses molecular biology methods to insert exogenous gene fragments into genes of phage-specific proteins such as gIII, expresses the exogenous gene-encoded protein or peptide by the phage, and presents them on the phage surface while maintaining the relative spatial structure and biological activity of the recombinant fusion proteins. The constructed diverse phage library is co-incubated with the target protein, and non-target protein-binding phage strains are removed by biopanning. With sufficient phage library capacity, phage clones with high affinity and high specificity can be obtained through multiple rounds of collection, amplification and enrichment. Gene sequencing can be used to identify the protein sequences encoded by these phage clones for further researches.

Phage antibody library is a diverse phage library formed by phage display of antibody genes. The quality of the phage antibody library is mainly determined by its capacity and diversity. In order to obtain high affinity antibodies, the phage antibody library needs to be as large as possible while maintaining diversity. The number of antibody fragments displayed on the phage surface represents the size of the library capacity, while the diversity of displayed fragments represents the antibody library diversity. Theoretically, the larger the library capacity of the phage antibody library, the higher the affinity of the antibody obtained by screening.

In this example, in order to avoid bias in the antibody library due to individual differences, and to ensure the diversity of the library as much as possible, 120 samples of total RNAs of mononuclear cells were obtained, collected and extracted from the peripheral blood and spleen of healthy adult individuals and from the umbilical cord blood of newborns. The RNA was reverse-transcribed to synthesize single-stranded cDNA, and then the VH, Vκ and VX, genes were amplified using variable region primers for different subgroups of antibodies, respectively. The amplification products were mixed in a certain ratio, and the heavy and light chain genes were respectively linked by PCR to form single chain antibodies (scFv), and cloned into phage plasmids by dual enzyme cleavage. SS320 *E. coli* competent cells were transformed by electroporation using the phage plasmids carrying the scFv genes. After SS320 proliferated to log phase, the helper phage was added for infection.

A natural antibody phage library with a library capacity of $1.2\times10^{12}$ and a positive rate of 88% was obtained. The gene family of the antibody library was found to be close to the natural distribution by sequencing randomly selected clones, and the number of amino acids in the CDR3 region was 3-20. No antibody repeats were found during the sequencing, and 88% of the gene sequences had the correct reading frames. The above results indicated that the phage antibody library had good diversity and had a high effective library capacity.

Example 2. Preparation of CLDN18.2-Stable Expression Cell Lines

In this example, a CHO cell line stably expressing CLDN18.2 (CHO-CLDN18.2) was prepared for use in cell-based phage display screening. The specific experimental procedure was as follows. The cDNA sequence of human CLDN18.2 was cloned into a pCDH lentiviral vector, and then co-transfected with a lentiviral packaging vector into 293t cells. After 48 or 72 hours of incubation, the cell supernatants enriched with lentiviral particles were collected and used for the direct infection with CHO cells, CT26 cells or SNU601 cells. The cells infected with lentivirus were subjected to screening and culture using puromycin, and after 2-3 weeks, the CLDN18.2 expression was tested by flow cytometry using CLDN18.2 specific antibody (IMAB362, Ganymed), the results are shown in FIG. 1.

The above results showed that CHO cells (named CHO-CLDN18.2 cell line), CT26 cells (CT26-CLDN18.2) and SNU601 cells (SNU601-CLDN18.2) stably expressing CLDN18.2 were obtained by lentiviral transfection and puromycin screening.

Example 3. Screening of Anti-CLDN18.2 Antibodies from Antibody Phage Display Libraries Three rounds of phage display library panning were performed using the CHO-CLDN18.2 stable expression cell line. The experimental procedure mainly refers to the following literature: Targeting membrane proteins for antibody discovery using phage display Jones M L et al., Scientific Reports 2016.

Figure 2:
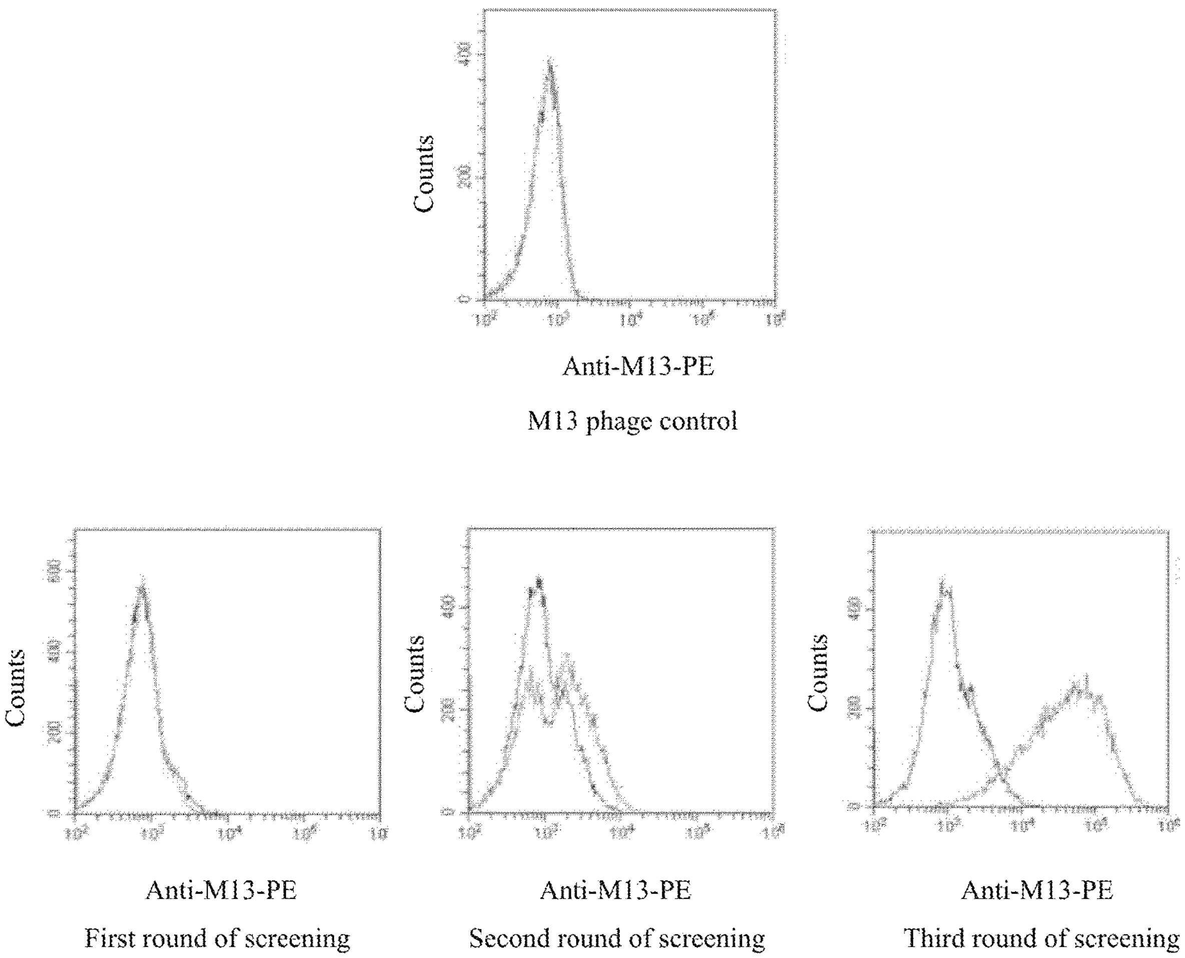
FIG. 2 shows the results of the binding of the control M13 phage and the phage library after the first, second and third rounds of screening to CHO cells and CHO-CLDN18.2 cells, as tested by flow cytometry.

The process is briefly described as follows. The phage library were incubated with CHO-K1 cells and the supernatant was taken after centrifugation. Then the supernatant was incubated with CHO-CLDN18.2 cells to allow the CLDN18.2 specific phages to bind to the cells. Cell precipitates were collected after centrifugation, and the cells were washed and collected. Then the phage library bound to the cells were eluted using 75 mM sodium citrate buffer. After neutralization of the phage library, the phage library after screening was amplified 100-fold using M13K07-assisted phage, followed by a second and a third round of screening in a similar manner to the first round of screening. The enrichment of phage was monitored by the initial phage amount of each round of screening and the phage titer collected after screening, and was tested by flow cytometry with the phage library and the CHO or CHO-CLDN18.2 stable expression cell lines. The results shown in FIG. 2 indicate that the phage display library can specifically bind to CHO-CLDN18.2 starting from the second round of enrichment screening, and its binding intensity increased with the number of screenings.

Figure 3:
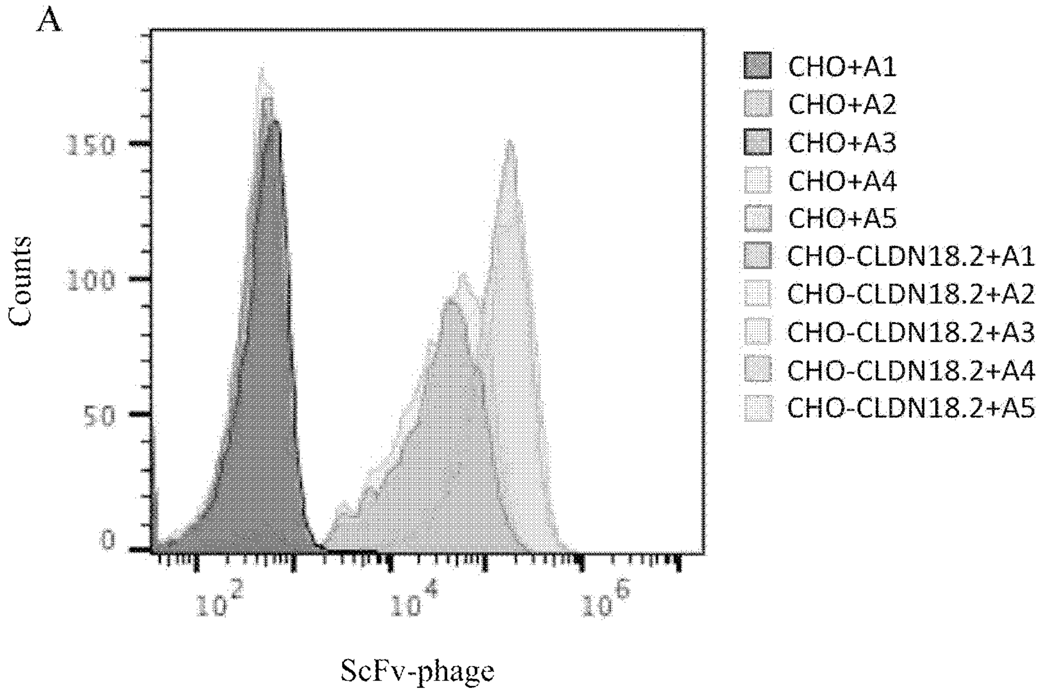
FIG. 3 shows the results of the binding of the screened phage clones A1, A2, A3, A4, and A5 (FIG. 3A) and A6 (FIG. 3B) to CHO cells and CHO-CLDN18.2 cells, as tested by flow cytometry.
Figure 3:
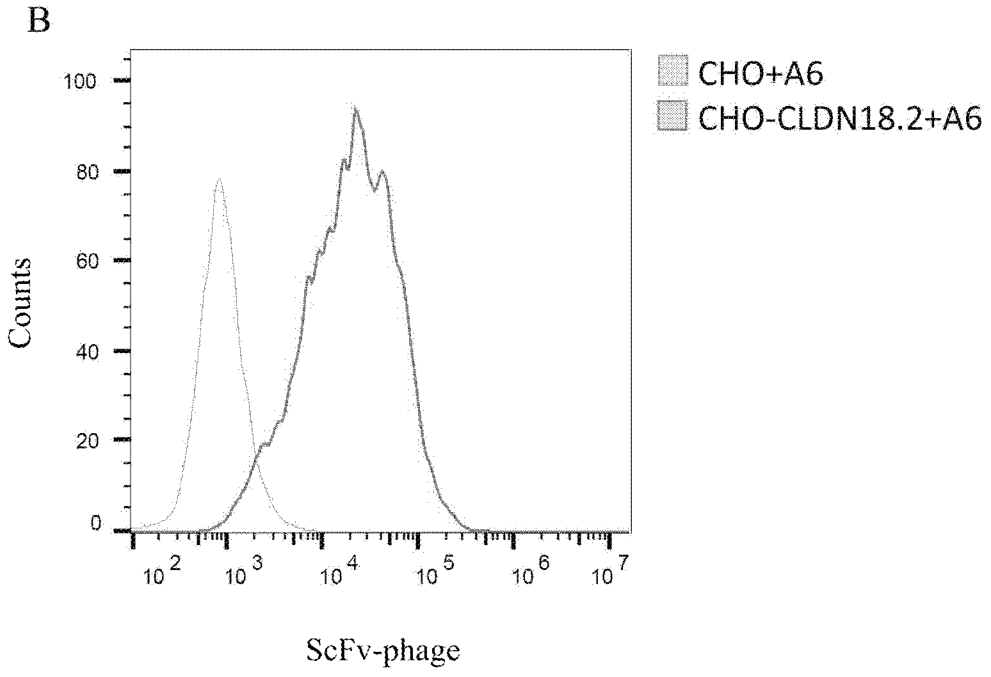

Enriched phage library was obtained after three rounds of screening. After infected by the library, the bacteria were spread on agarose plates for culture. The monoclonal colonies were picked and placed in a 96-well deep-well plate with 2YT medium containing ampicillin and kanamycin, and were cultured with shaking at 37° C. to obtain supernatants containing monoclonal phages. The monoclonal phage supernatants were incubated with CHO-CLDN18.2 cells or CT26-CLDN18.2 cells at 4° C. for 1 h, followed by washing with PBS (flow cytometry buffer) containing 1 mM EDTA and 0.5% BSA. PE-labeled anti-M13 antibody (purchased from Yiqiao Shenzhou) was added and was incubated at 4° C. for 30 min. Subsequently, the binding of phages to cells was tested by flow cytometry, and the results are shown in FIG. 3.

The above results indicated that the screened monoclonal phages A1 to A6 could all bound well to CHO-CLDN18.2 cells but not to CHO control cells.

Example 4. Preparation of Recombinant Antibodies

The cDNA sequences of the heavy and light chain variable regions of the monoclonal phages were cloned into pcDNA3.4 vectors (Invitrogen) which already contained the antibody constant region, respectively, and a total of 6 plasmids expressing monoclonal antibody heavy and light chain were obtained. The plasmids were transiently transfected into EXPI-293 cells (Invitrogen) using the PEI method for 7-10 days and centrifuged and supernatants were collected. The supernatants were purified by protein A to obtain purified antibodies. The 6 monoclonal antibodies above were named 18.2-A1 (A1), 18.2-A2 (A2), 18.2-A3 (A3), 18.2-A4 (A4), 18.2-A5 (A5) and 18.2-A6 (A6). The amino acid sequences and the coding sequences of the heavy and light chain variable regions of these antibodies are shown in Tables 1 and 2 below, and the CDR sequences of the antibodies determined according to the Kabat CDR system are shown in Table 3. The sequences of the heavy and light chain constant regions of the recombinant antibodies are shown in Table 4.

TABLE 1

VH and VL sequences of CLDN18.2 antibodies

| | | |
|---|---|---|
| 18.2-A1 (A1)<br>Heavy Chain<br>Variable Region | EVQLVQSGAEVKKPGASVKVSCKASGYTFTSSWLIWVRQAPG<br>QGLEWIGTIVPSDSYTNYNQKFKDRATLTVDKSTSTAYMELS<br>SLRSEDTAVYYCTRFRTGNSFDYWGQGTLVTVSS | SEQ ID NO: 1 |
| 18.2-A1 (A1)<br>Light Chain<br>Variable Region | DIVMTQSPDSLSVGLGERATINCKSSQSVLNSGNQKNYLTWY<br>QQKPGQPPKLLIYWAVARQSGVPDRFSGSGSGTDFTLTISSL<br>QAEDVAVYYCQNSIAYPFTFGQGTKVEIK | SEQ ID NO: 6 |
| 18.2-A2 (A2)<br>Heavy Chain<br>Variable Region | EVQLVQSGAEVKKPGASVKVSCKASGYTFTSFWVGWVRQAPG<br>QGLEWIGNVSPSDSYTNYNQKFKDRATLTVDKSTSTAYMELS<br>SLRSEDTAVYYCTRLSSGNSFDYWGQGTLVTVSS | SEQ ID NO: 11 |
| 18.2-A2 (A2)<br>Light Chain<br>Variable Region | DIVMTQSPDSLSVSLGERATINCKSSQSVLNSGNQKNYLTWY<br>QQKPGQPPKLLIYWSSTKQSGVPDRFSGSGSGTDFTLTISSL<br>QAEDVAVYYCQNAFSFPFTFGQGTKVEIK | SEQ ID NO: 16 |
| 18.2-A3 (A3)<br>Heavy Chain<br>Variable Region | EVQLVQSGAEVKKPGASVKVSCKASGYTFTSYWLNWVRQAPG<br>QGLEWIGSMYPSDSYTNYNQKFKDRATLTVDKSTSTAYMELS<br>SLRSEDTAVYYCTRFSRGNSFDYWGQGTLVTVSS | SEQ ID NO: 21 |
| 18.2-A3 (A3)<br>Light Chain<br>Variable Region | DIVMTQSPDSLTVALGERATINCKSSQSLLESGNQKNYLTWY<br>QQKPGQPPKLLIYWSWAKNSGVPDRFSGSGSGTDFTLTISSL<br>QAEDVAVYYCQNAYAFPFTFGQGTKVEIK | SEQ ID NO: 26 |
| 18.2-A4 (A4)<br>Heavy Chain<br>Variable Region | EVQLVQSGAEVKKPGASVKVSCKASGYTFTSFWISWVRQAPG<br>QGLEWIGNILPSDSYTNYNQKFKDRATLTVDKSTSTAYMELS<br>SLRSEDTAVYYCTRYWRGNSFDYWGQGTLVTVSS | SEQ ID NO: 31 |
| 18.2-A4 (A4)<br>Light Chain<br>Variable Region | DIVMTQSPDSLALALALGERATINCKSSQSIINSGNQKNYLT<br>WYQQKPGQPPKLLIYWGGTRHSGVPDRFSGSGSGTDFTLTIS<br>SLQAEDVAVYYCQNGYYSPFTFGQGTKVEIK | SEQ ID NO: 36 |
| 18.2-A5 (A5)<br>Heavy Chain<br>Variable Region | EVQLVQSGAEVKKPGASVKVSCKASGYTFTSSWVGWVRQAPG<br>QGLEWIGNSYPSDSYTNYNQKFKDRATLTVDKSTSTAYMELS<br>SLRSEDTAVYYCTRLGRGNSFDYWGQGTLVTVSS | SEQ ID NO: 41 |
| 18.2-A5 (A5)<br>Light Chain<br>Variable Region | DIVMTQSPDSLTVALGERATINCKSSQSLIHSGNQKNYLTWY<br>QQKPGQPPKLLIYWGLSKNSGVPDRFSGSGSGTDFTLTISSL<br>QAEDVAVYYCQNSIYYPFTFGQGTKVEIK | SEQ ID NO: 46 |
| 18.2-A6 (A6)<br>Heavy Chain<br>Variable Region | EVQLVQSGAEVKKPGASVKVSCKASGYTFTSYWLGWVRQAPG<br>QGLEWIGHYPSDSYTNYNQKFKDRATLTVDKSTSTAYMELSS<br>LRSEDTAVYYCTRFWRGNSFDYWGQGTLVTVSS | SEQ ID NO: 55 |
| 18.2-A6 (A6)<br>Light Chain<br>Variable Region | DIVMTQSPDSLTIGLGERATINCKSSQSLLNSGNQKNYLTWY<br>QQKPGQPPKLLIYWAAGKESGVPDRFSGSGSGTDFTLTISSL<br>QAEDVAVYYCQNGYSHPFTFGQGTKVEIK | SEQ ID NO: 60 |

TABLE 2

Coding sequences of VH and VL of CLDN18.2 antibodies

| | | |
|---|---|---|
| 18.2-A1 (A1)<br>Heavy Chain<br>Variable Region | GAGGTCCAACTCGTTCAATCTGGAGCAGAGGTAAAAAAGCCTGG<br>AGCCAGCGTCAAGGTTAGTTGTAAGGCATCTGGTTACACCTTTA<br>CCAGCTCTTGGCTCATTTGGGTGCGCCAGGCACCTGGTCAGGGA<br>TTGGAATGGATTGGCACTATCGTCCCCTCTGACTCTTACACCAA<br>CTACAATCAGAAATTTAAAGATCGCGCCACTTTGACAGTCGATA<br>AGTCTACGAGTACGGCTTATATGGAGCTCAGTTCCCTGCGCAGC<br>GAGGACACAGCCGTCTATTACTGCACCCGCTTCAGGACCGGTAA<br>CAGCTTTGACTACTGGGGACAAGGTACATTGGTTACGGTCAGCT<br>CT | SEQ ID NO: 2 |
| 18.2-A1 (A1)<br>Light Chain<br>Variable Region | GACATCGTTATGACTCAGTCTCCCGACTCCCTCAGCGTCGGCTT<br>GGGTGAACGCGCCACTATCAATTGTAAGTCCAGTCAGTCCGTCC<br>TCAATTCCGGGAATCAGAAGAACTACCTTACATGGTATCAGCAG<br>AAACCTGGTCAGCCACCAAAATTGCTCATCTATTGGGCCGTGGC<br>CAGGCAGAGCGGCGTGCCCGACCGCTTTAGTGGGAGCGGCTCTG<br>GCACAGATTTTACACTTACTATTAGTAGTCTTCAGGCCGAGGAT<br>GTCGCGGTATATTACTGTCAGAATAGCATAGCCTATCCCTTTAC<br>CTTCGGTCAGGGAACGAAGGTTGAAATCAAG | SEQ ID NO: 7 |

TABLE 2-continued

| Coding sequences of VH and VL of CLDN18.2 antibodies | | |
|---|---|---|
| 18.2-A2 (A2) Heavy Chain Variable Region | GAGGTCCAACTCGTTCAATCTGGAGCAGAGGTAAAAAAGCCTGG AGCCAGCGTCAAGGTTAGTTGTAAGGCATCTGGTTACACCTTTA CCAGCTTTTGGGTCGGTTGGGTGCGCCAGGCACCTGGTCAGGGA TTGGAATGGATTGGCAATGTCTCCCCCTCTGACTCTTACACCAA CTACAATCAGAAATTTAAAGATCGCGCCACTTTGACAGTCGATA AGTCTACGAGTACGGCTTATATGGAGCTCAGTTCCCTGCGCAGC GAGGACACAGCCGTCTATTACTGCACCCGCTTATCAAGCGGTAA CAGCTTTGACTACTGGGGACAAGGTACATTGGTTACGGTCAGCT CT | SEQ ID NO: 12 |
| 18.2-A2 (A2) Light Chain Variable Region | GACATCGTTATGACTCAGTCTCCCGACTCCCTCAGCGTCAGCTT GGGTGAACGCGCCACTATCAATTGTAAGTCCAGTCAGTCCGTCC TCAATTCCGGGAATCAGAAGAACTACCTTACATGGTATCAGCAG AAACCTGGTCAGCCACCAAAATTGCTCATCTATTGGAGCTCGAC CAAGCAGAGCGGCGTGCCCGACCGCTTTAGTGGGAGCGGCTCTG GCACAGATTTTACACTTACTATTAGTAGTCTTCAGGCCGAGGAT GTCGCGGTATATTACTGTCAGAATGCCTTTTCGTTCCCCTTTAC CTTCGGTCAGGGAACGAAGGTTGAAATCAAG | SEQ ID NO: 17 |
| 18.2-A3 (A3) Heavy Chain Variable Region | GAGGTCCAACTCGTTCAATCTGGAGCAGAGGTAAAAAAGCCTGG AGCCAGCGTCAAGGTTAGTTGTAAGGCATCTGGTTACACCTTTA CCAGCTATTGGCTCAATTGGGTGCGCCAGGCACCTGGTCAGGGA TTGGAATGGATTGGCAGTATGTATCCCTCTGACTCTTACACCAA CTACAATCAGAAATTTAAAGATCGCGCCACTTTGACAGTCGATA AGTCTACGAGTACGGCTTATATGGAGCTCAGTTCCCTGCGCAGC GAGGACACAGCCGTCTATTACTGCACCCGCTTCAGCCGCGGCAA CAGCTTTGACTACTGGGGACAAGGTACATTGGTTACGGTCAGCT CT | SEQ ID NO: 22 |
| 18.2-A3 (A3) Light Chain Variable Region | GACATCGTTATGACTCAGTCTCCCGACTCCCTCACCGTCGCCTT GGGTGAACGCGCCACTATCAATTGTAAGTCCAGTCAGTCCCTCC TCGAGTCCGGGAATCAGAAGAACTACCTTACATGGTATCAGCAG AAACCTGGTCAGCCACCAAAATTGCTCATCTATTGGAGCTGGGC CAAGAATAGCGGCGTGCCCGACCGCTTTAGTGGGAGCGGCTCTG GCACAGATTTTACACTTACTATTAGTAGTCTTCAGGCCGAGGAT GTCGCGGTATATTACTGTCAGAATGCTTATGCATTTCCCTTTAC CTTCGGTCAGGGAACGAAGGTTGAAATCAAG | SEQ ID NO: 27 |
| 18.2-A4 (A4) Heavy Chain Variable Region | GAGGTCCAACTCGTTCAATCTGGAGCAGAGGTAAAAAAGCCTGG AGCCAGCGTCAAGGTTAGTTGTAAGGCATCTGGTTACACCTTTA CCAGCTTTTGGATCAGTTGGGTGCGCCAGGCACCTGGTCAGGGA TTGGAATGGATTGGCAACATTCTCCCCTCTGACTCTTACACCAA CTACAATCAGAAATTTAAAGATCGCGCCACTTTGACAGTCGATA AGTCTACGAGTACGGCTTATATGGAGCTCAGTTCCCTGCGCAGC GAGGACACAGCCGTCTATTACTGCACCCGCTACTGGCGCGGCAA CAGCTTTGACTACTGGGGACAAGGTACATTGGTTACGGTCAGCT CT | SEQ ID NO: 32 |
| 18.2-A4 (A4) Light Chain Variable Region | GACATCGTTATGACTCAGTCTCCCGACTCCCTCGCCCTCGCCTT GGGTGAACGCGCCACTATCAATTGTAAGTCCAGTCAGTCCATCA TCAATTCCGGGAATCAGAAGAACTACCTTACATGGTATCAGCAG AAACCTGGTCAGCCACCAAAATTGCTCATCTATTGGGGCGGGAC CAGGCATAGCGGCGTGCCCGACCGCTTTAGTGGGAGCGGCTCTG GCACAGATTTTACACTTACTATTAGTAGTCTTCAGGCCGAGGAT GTCGCGGTATATTACTGTCAGAATGGCTATTACTCTCCCTTTAC CTTCGGTCAGGGAACGAAGGTTGAAATCAAG | SEQ ID NO: 37 |
| 18.2-A5 (A5) Heavy Chain Variable Region | GAGGTCCAACTCGTTCAATCTGGAGCAGAGGTAAAAAAGCCTGG AGCCAGCGTCAAGGTTAGTTGTAAGGCATCTGGTTACACCTTTA CCAGCTCTTGGGTCGGTTGGGTGCGCCAGGCACCTGGTCAGGGA TTGGAATGGATTGGCAATAGCTACCCCTCTGACTCTTACACCAA CTACAATCAGAAATTTAAAGATCGCGCCACTTTGACAGTCGATA AGTCTACGAGTACGGCTTATATGGAGCTCAGTTCCCTGCGCAGC GAGGACACAGCCGTCTATTACTGCACCCGCTTGGGGCGCGGCAA CAGCTTTGACTACTGGGGACAAGGTACATTGGTTACGGTCAGCT CT | SEQ ID NO: 42 |
| 18.2-A5 (A5) Light Chain Variable Region | GACATCGTTATGACTCAGTCTCCCGACTCCCTCACCGTCGCCTT GGGTGAACGCGCCACTATCAATTGTAAGTCCAGTCAGTCCCTCA TCCATTCCGGGAATCAGAAGAACTACCTTACATGGTATCAGCAG AAACCTGGTCAGCCACCAAAATTGCTCATCTATTGGGGCTTGAG CAAGAATAGCGGCGTGCCCGACCGCTTTAGTGGGAGCGGCTCTG GCACAGATTTTACACTTACTATTAGTAGTCTTCAGGCCGAGGAT GTCGCGGTATATTACTGTCAGAATAGCATTTACTATCCCTTTAC CTTCGGTCAGGGAACGAAGGTTGAAATCAAG | SEQ ID NO: 47 |

TABLE 2-continued

| Coding sequences of VH and VL of CLDN18.2 antibodies | | |
|---|---|---|
| 18.2-A6 (A6) Heavy Chain Variable Region | GAGGTCCAACTCGTTCAATCTGGAGCAGAGGTAAAAAAGCCTGG AGCCAGCGTCAAGGTTAGTTGTAAGGCATCTGGTTACACCTTTA CCAGCTATTGGCTCGGTTGGGTGCGCCAGGCACCTGGTCAGGGA TTGGAATGGATTGGCATTATATACCCCTCTGACTCTTACACCAA CTACAATCAGAAATTTAAAGATCGCGCCACTTTGACAGTCGATA AGTCTACGAGTACGGCTTATATGGAGCTCAGTTCCCTGCGCAGC GAGGACACAGCCGTCTATTACTGCACCCGCTTCTGGCGCGGTAA CAGCTTTGACTACTGGGGACAAGGTACATTGGTTACGGTCAGCT CT | SEQ ID NO: 56 |
| 18.2-A6 (A6) Light Chain Variable Region | GACATCGTTATGACTCAGTCTCCCGACTCCCTCACCATCGGCTT GGGTGAACGCGCCACTATCAATTGTAAGTCCAGTCAGTCCCTCC TCAATTCCGGGAATCAGAAGAACTACCTTACATGGTATCAGCAG AAACCTGGTCAGCCACCAAAATTGCTCATCTATTGGGCCGCGGG CAAGGAGAGCGGCGTGCCCGACCGCTTTAGTGGGAGCGGCTCTG GCACAGATTTTACACTTACTATTAGTAGTCTTCAGGCCGAGGAT GTCGCGGTATATTACTGTCAGAACGGGTATTCCCATCCCTTTAC CTTCGGTCAGGGAACGAAGGTTGAAATCAAG | SEQ ID NO: 61 |

TABLE 3

Kabat CDR sequences of antibodies

| 6666 | CDR H1 | CDR H2 | CDR H3 | CDR L1 | CDR L2 | CDR L3 |
|---|---|---|---|---|---|---|
| 18.2-A1 (A1) | SSWLI | TIVPSDSYTNYNQKFKD | FRTGNSFDY | KSSQSVLNSGNQKNYLT | WAVARQS | QNSIAYPFT |
| 18.2-A2 (A2) | SFWVG | KVSPSDSYTNYKQKFKD | LSSGNSFDY | KSSQSVLNSGNQKNYLT | WSSTKQS | QNAFSFPFT |
| 18.2-A3 (A3) | SYWLN | SMYPSDSYTNYNQKFKD | FSRGNSFDY | KSSQSLLESGNQKNYLT | WSWAKNS | QNAYAFPFT |
| 18.2-A4 (A4) | SFWIS | NILPSDSYTNYNQKFKD | YWRGNSFDY | KSSQSIINSGNQKNYLT | WGGTRHS | QNGYYSPFT |
| 18.2-A5 (A5) | SSWVG | NSYPSDSYTNYNQKFKD | LGRGNSFDY | KSSQSLIHSGNQKNYLT | WGLSKNS | QNSIYYPFT |
| 18.2-A6 (A5) | SYWLG | IIYPSDSYTNYNQKFKD | FWRGNSFDY | KSSQSLLESGNQKNYLT | WAAGKES | QNGYSHPFT |

TABLE 4

| Sequences of heavy and light chain constant regions of recombinant antibodies | | |
|---|---|---|
| Sequence of heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPELLGGPSVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPGK | SEQ ID NO: 51 |
| Coding sequence of heavy chain constant region | GCGAGCACCAAGGGCCCATCGGTCTTCCCCCTGGCACCCTCC TCCAAGAGCACCTCTGGGGGCACAGCGGCCCTGGGCTGCCTG GTCAAGGACTACTTCCCCGAACCGGTGACGGTGTCGTGGAAC TCAGGCGCCCTGACCAGCGGCGTGCACACCTTCCCGGCTGTC CTACAGTCCTCAGGACTCTACTCCCTCAGCAGCGTGGTGACT GTGCCCTCTAGCAGCTTGGGCACCCAGACCTACATCTGCAAC GTGAATCACAAGCCCAGCAACACCAAGGTGGACAAGAAAGTT GAGCCCAAATCTTGTGACAAAACTCACACATGCCCACCGTGC CCAGCACCTGAACTCCTGGGGGGACCGTCAGTCTTCCTCTTC CCCCCAAAACCCAAGGACACCCTCATGATCTCCCGGACCCCT GAGGTCACATGCGTGGTGGTGGACGTGAGCCACGAAGACCCT | SEQ ID NO: 52 |

TABLE 4-continued

| Sequences of heavy and light chain constant regions of recombinant antibodies | | |
|---|---|---|
| | GAGGTCAAGTTCAACTGGTACGTGGACGGCGTGGAGGTGCAT<br>AATGCCAAGACAAAGCCGCGGGAGGAGCAGTACAACAGCACG<br>TACCGTGTGGTCAGCGTCCTCACCGTCCTGCACCAGGACTGG<br>CTGAATGGCAAGGAGTACAAGTGCAAGGTCTCCAACAAAGCC<br>CTCCCAGCCCCCATCGAGAAAACCATCTCCAAAGCCAAAGGG<br>CAGCCCCGAGAACCACAGGTGTACACCCTGCCCCCATCCCGG<br>GAAGAGATGACCAAGAACCAGGTCAGCCTGACCTGCCTGGTC<br>AAAGGCTTCTATCCCAGCGACATCGCCGTGGAGTGGGAGAGC<br>AATGGGCAGCCGGAGAACAACTACAAGACCACGCCTCCCGTG<br>CTGGACTCCGACGGCTCCTTCTTCCTCTACAGCAAGCTCACC<br>GTGGACAAGAGCAGGTGGCAGCAGGGGAACGTCTTCTCATGC<br>TCCGTGATGCATGAGGCTCTGCACAACCACTACACGCAGAAG<br>AGCCTCTCCCTGTCTCCGGGTAAATGA | |
| Sequence of light chain constant region | RTVAAPSVFIFPPSDEQLKSGTASVVCLLNNFYPREAKVQWK<br>VDNALQSGNSQESVTEQDSKDSTYSLSSTLTLSKADYEKHKV<br>YACEVTHQGLSSPVTKSFNRGEC | SEQ ID NO: 53 |
| Coding sequence of light chain constant region | CGGACCGTGGCAGCACCAAGTGTCTTCATCTTCCCGCCATCT<br>GATGAGCAGTTGAAATCTGGAACTGCTTCTGTTGTGTGCCTG<br>CTGAATAACTTCTATCCCAGAGAGGCCAAAGTACAGTGGAAG<br>GTGGATAACGCCCTCCAATCGGGTAACTCCCAGGAGAGTGTC<br>ACAGAGCAGGACAGCAAGGACAGCACCTACAGCCTCAGCAGC<br>ACCCTGACGCTGAGCAAAGCAGACTACGAGAAACACAAAGTC<br>TACGCCTGCGAAGTCACCCATCAGGGCCTGAGCTCGCCCGTC<br>ACAAAGAGCTTCAACAGGGGAGAGTGTTAA | SEQ ID NO: 54 |

Example 5. Tests for the Binding Activities of Recombinant Monoclonal Antibodies Binding activities of the recombinant monoclonal antibodies to CLDN18.2 were determined. Specifically, well-grown cell lines stably expressing CT26-CLDN18.2 were taken. The cells were washed with PBS, mixed with the fold-diluted antibody and incubated at 4° C. for 1 hour. The cells were washed once with flow cytometry buffer, PE-labeled anti-human IgG antibody was added, and incubated at 4° C. for 30 minutes. The supernatant was removed by centrifugation, and after the cells were washed with flow cytometry buffer, the fluorescence intensity on the surface of the cells was tested by flow cytometry. The relative binding activity of each antibody was calculated using the average fluorescence intensity.

Figure 4:
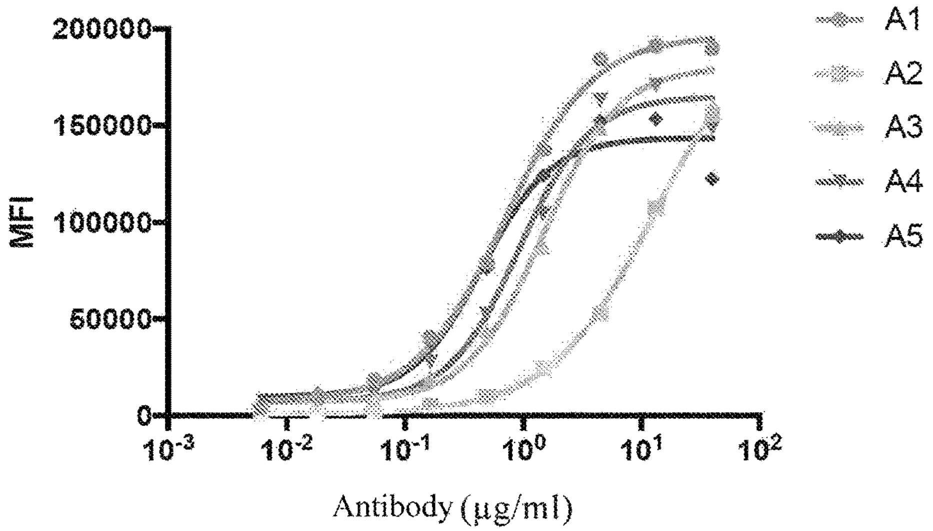
FIG. 4 shows the results of the binding of the recombinant antibodies 18.2-A1, 18.2-A2, 18.2-A3, 18.2-A4, 18.2-A5 (FIG. 4A), 18.2-A5F and 18.2-A6F (FIG. 4B) with different concentrations to CT26-CLDN18.2 cells, and the EC50 values, as tested by flow cytometry.
Figure 4:
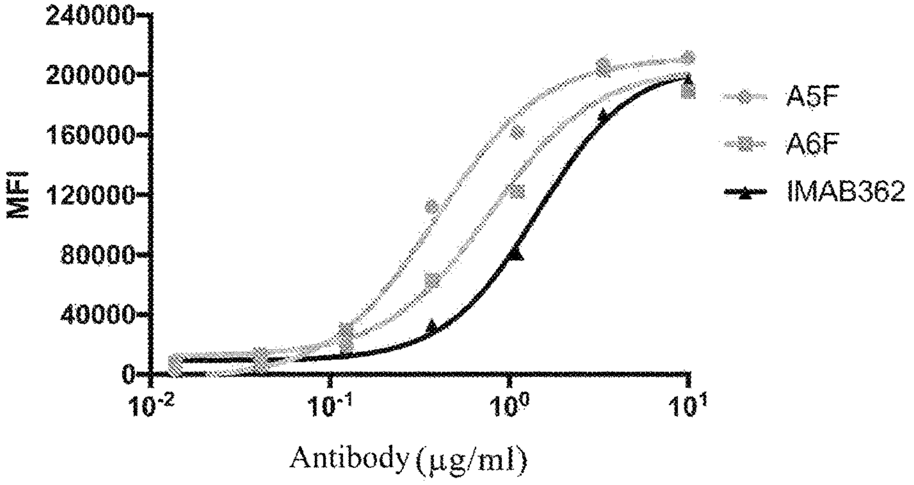

18.2-A1 (A1), 18.2-A2 (A2), 18.2-A3 (A3), 18.2-A4 (A4) 18.2-A5 (A5) and 18.2-A6 (A6) antibodies did not bind to the control CT26 cell line (results are not shown), but were able to bind well to the CT26 cell line expressing CLDN18.2, as shown in FIG. 4. The average fluorescence intensity of CT26-CLDN18.2 gradually decreased with the dilution of the antibody. The relative binding activities (EC50) of the above CLDN18.2 antibodies are also shown in FIG. 4.

Example 6. Tests for the Binding Specificity of Recombinant Antibodies

Human Claudin18 proteins include two homologues, i.e., CLDN18.1 and CLDN18.2, which share exons other than exon 1, and the exon 1 sequences of CLDN18.1 and CLDN18.2 are highly similar with only 8 different amino acids in the first extracellular region. The exon 1 of CLDN18.1 and the exon 1 of CLDN18.2 are specifically expressed in different tissues driven by different promoters. Among them, CLDN18.1 is specifically expressed in lung epithelial cells, while CLDN18.2 is specifically expressed in gastric epithelial cells. To identify the specificity of the screened CLDN18.2 antibodies, binding of the antibodies to CLDN18.1 and CLDN18.2 was tested.

Specifically, well-grown 293t cells were taken to transiently express flag-tagged CLDN18.1 (CLDN18.1-Flag) or CLDN18.2 (CLDN18.2-Flag). 48 hours after transfection, the cells were digested with trypsin. After washed with flow cytometry buffer, the cells were mixed with 10 μg/ml of isotype control antibody or one of the above five CLDN18.2 antibodies in 200 μl of flow cytometry buffer, and were incubated at 4° C. for 1 hour. Subsequently, the cells were washed once with flow cytometry buffer, PE-labeled anti-human IgG antibody was added, and incubated at 4° C. for 30 min. The supernatant was removed by centrifugation, wash was performed twice with flow cytometry buffer, and the cells were fixed in a fix solution containing 1% paraformaldehyde and 0.5% triton-X100 and the cell membrane was permeabilized. Subsequently, the cells were incubated with APC-labeled anti-flag antibody for 30 min and tested by flow cytometry.

Figure 5:
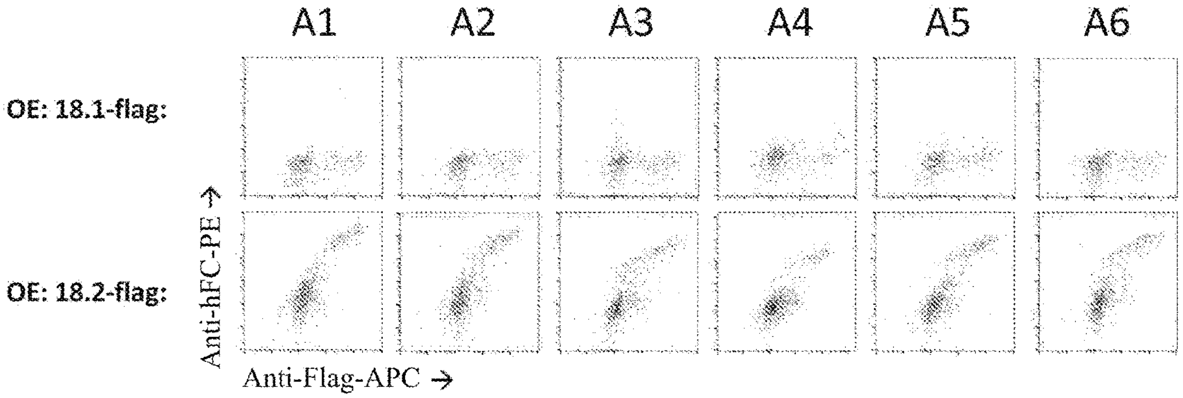
FIG. 5 shows the results of the binding of the CLDN18.2 antibodies to 293t cells expressing CLDN18.1 (18.1-flag) or CLDN18.2 (18.2-flag) as tested by flow cytometry.

The results are shown in FIG. 5. Flag-positive cell population could be detected in 293t cells exogenously expressing CLDN18.1-flag or CLDN18.2-flag, showing that the transfected CLDN18.1 or CLDN18.2 proteins were well expressed in the cells, with the positive expression rate of around 20%. CLDN18.2 antibodies 18.2-A1, 18.2-A2, 18.2-A3, 18.2-A4, 18.2-A5 and 18.2-A6 were able to bind well to CLDN18.2-flag transfected positive 293t cells, but none of the six antibodies bound to CLDN18.1-positive cells. The above results indicated that all the six CLDN18.2 antibodies were able to specifically bind to CLDN18.2 but not to CLDN18.1.

Example 7. Tests for Endocytosis of CLDN18.2 Antibody after Binding to Cells

It has been reported that the binding of some antibodies to cell surface antigens can cause endocytosis of antigen and antibody complexes, thereby reducing the expression level of the cell surface antigens and accelerating antibody metabolism in vivo (Schrama D et al., 2006, Nat Rev Drug Discov). In this example, the ability of antibodies 18.2-A1, 18.2-A3, 18.2-A4 and 18.2-A6 to be endocytosed by cells was tested in SNU601 cells stably expressing CLDN18.2. Specifically, the CLDN18.2 antibodies 18.2-A1, 18.2-A3, 18.2-A4, 18.2-A6 or IMAB362 antibody (as described in Example 2) at a concentration of 10 μg/ml, blank control (PBS) and isotype control (ISO) were incubated with the cells for 4 h at 4° C. or 37° C., respectively. Subsequently, they were washed at 4° C. and stained with PE-labeled anti-human IgG antibody. After fixation with 4% formalin, antibody binding on the cell surface was tested by flow cytometry.

Figure 6:
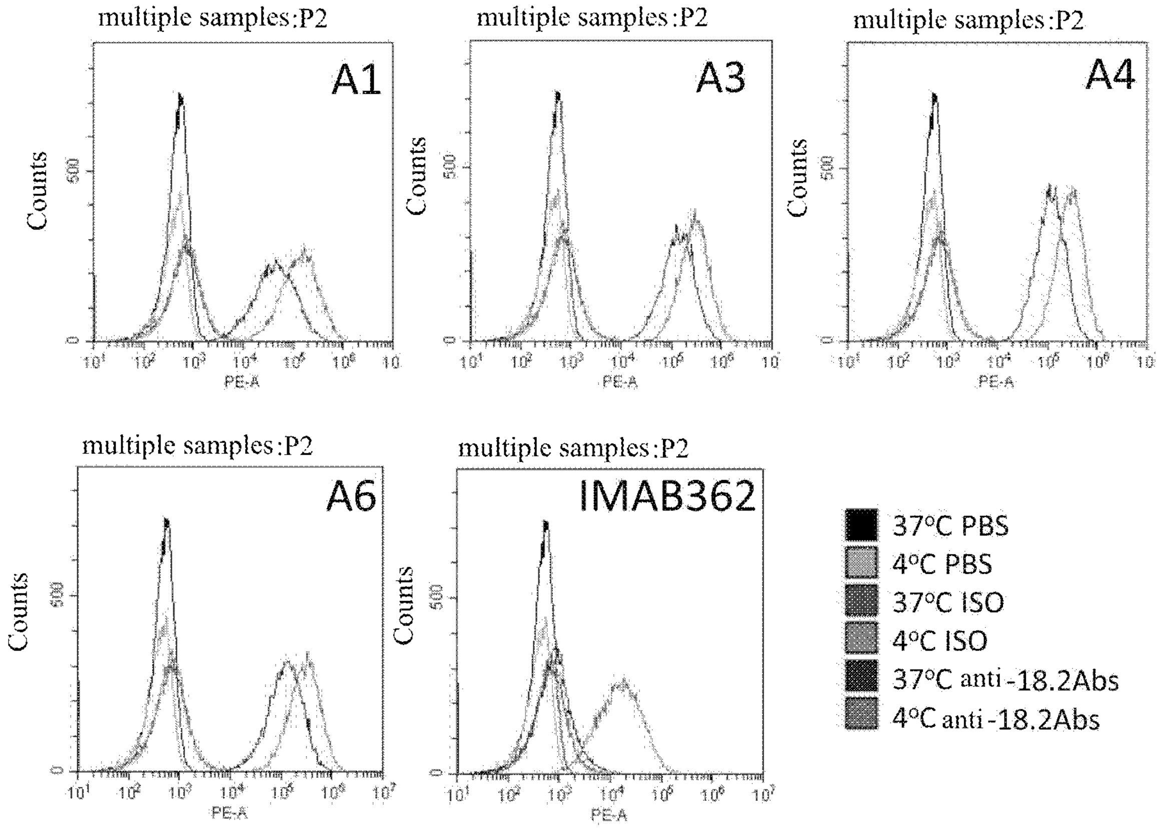
FIG. 6 shows the results of the binding of the CLDN18.2 antibodies to the surface of SNU601 cells expressing CLDN18.2, and the endocytosis by the cells under the incubation conditions of 4° C. and 37° C.

As shown in the results in FIG. 6, the IMAB362 antibody and 18.2-A1, 18.2-A3, 18.2-A4 and 18.2-A6 antibodies all bound well to SNU601 cells expressing CLDN18.2 under 4° C. incubation condition. However, under 37° C. incubation condition, IMAB362 antibody was endocytosed by the cells and the antibody staining on the cell surface decreased significantly; whereas 18.2-A1, 18.2-A3, 18.2-A4 and 18.2-A6 antibodies did not undergo significant endocytosis and still bound well to the cells under 37° C. condition.

The above results indicated that IMAB362 antibody could induce cellular endocytosis, which may down-regulate the expression level of CLDN18.2 antigen on the cell surface. In vivo, endocytosis could also cause alteration in antibody metabolism, and accelerate the rate of antibody clearance in vivo. In contrast, the CLDN18.2 antibodies of the present disclosure did not cause significant cellular endocytosis and thus did not down-regulate the level of the target antigen CLDN18.2 on the cell surface, nor did they affect the antibody metabolism in vivo.

Example 8. Preparation and Purification of Defucosylated Antibodies

The defucosylated forms of the CLDN18.2 antibodies were further prepared. Specifically, the heavy and light chain coding sequences of the antibody were cloned into a mammalian GS expression vector capable of stable expression, with both the heavy and light chain coding sequences driven by the CMV promoter. The expression vector was transfected into CHO-K1 cells domesticated in serum-free and suspension culture and the domesticated CHO-K1 cell line with Fut8 gene knockout. Stable expression cell lines were screened and selected using MSX. After stable expression cell lines were obtained, they were cultured in shake flasks for 12-14 days, supplemented with supplemental medium in between as needed.

Subsequently, the culture supernatant was collected, and after filtering, the expressed antibodies were captured through a protein A chromatography column. The antibodies were eluted and dialyzed with PBS to obtain purified antibodies. Among them, the 18.2-A1, 18.2-A2, 18.2-A3, 18.2-A4, 18.2-A5 and 18.2-A6 antibodies expressed in the CHO-K1 cell line with Fut8 gene knockout were named 18.2-A1F, 18.2-A2F, 18.2-A3F, 18.2-A4F, 18.2-A5F and 18.2 A6F.

Example 9. Characterization of Glycosylation Modification of Defucosylated Antibodies Subsequently, the glycosylation modification of the defucosylated antibodies expressed in the CHO-K1 cell line with Fut8 gene knockout and the common antibodies produced in the CHO-K1 cells were analyzed. The glycosyls of the antibodies were obtained by digesting 100 μg of the antibodies by trypsin and glycopeptidase followed by purification, and were subjected to fluorescence tandem mass spectrometry analysis. The identification of various glycosyls relies on their mass-to-charge ratio m/z, and the percentage of glycosyl groups was calculated from the percentage of area tested by fluorescence.

Glycosyl Nomenclature:

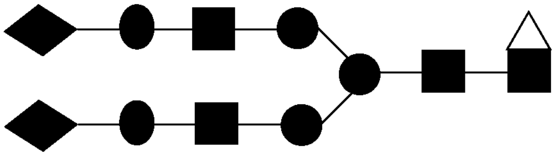

♦ N-Acetylneuraminic acid ■ N-Acetylgalactosamine △ Fucose ● Mannose ● Galactose ◈ N-Hydroxyacetylneuraminic acid Definition of glycosyl numbering: 5 numbers respectively express the numbers of various sugars: six-carbon sugar (galactose, mannose, or glucose), N-acetylhexosamine (GlcNA or GalNAc), fucose (abbreviated as FUC), N-acetylneuraminic acid (Neu5Ac), and N-hydroxyacetylneuraminic acid (Neu5Gc). Among these, the third number indicates the number of fucose. As shown in Table 4 below:

TABLE 4

Glycosyl numberings and heir corresponding carbohydrate chains

| Mass-to-charge Ratio | Glycosyl Numbering | Possible Carbohydrate Chain |
|---|---|---|
| 1425.59 | 33000 | 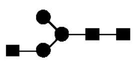 and/or 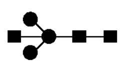 |
| 1546.62 | 52000 | 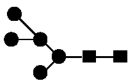 |
| 1571.65 | 33100 | 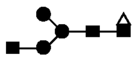 and/or 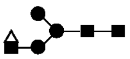 |
| 1628.67 | 34000 | 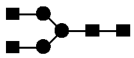 and/or 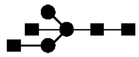 |

TABLE 4-continued

| Glycosyl numberings and heir corresponding carbohydrate chains | | |
|---|---|---|
| Mass-to-charge Ratio | Glycosyl Numbering | Possible Carbohydrate Chain |
| 1774.73 | 34100 | 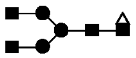 |
| 1790.72 | 44000 | 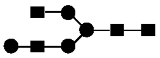 and/or 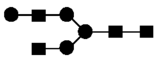 |
| 1831.75 | 35000 | 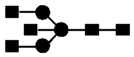 and/or 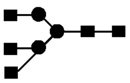 |
| 1936.78 | 44100 | 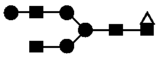 |
| 1952.77 | 54000 | 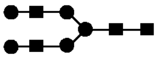 |
| 2098.83 | 54100 | 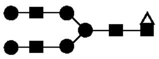 and/or 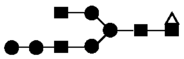 |
| 2081.82 | 44010 | 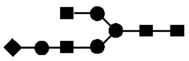 |
| 2243.88 | 54010 | 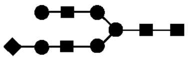 |
| 2259.87 | 54001 | 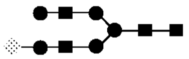 |
| 2534.97 | 54020 | 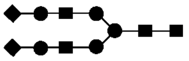 |

The analytical results of the carbohydrate chains of the Claudin18.2-A1 antibodies produced in the CHO-K1 cells are shown in Table 5 below:

TABLE 5

| Analytical results of the carbohydrate chains of the Claudin18.2 antibodies | | |
|---|---|---|
| Glycosyl Numbering | Fucose | percentage % |
| 33000 | no | 0.2 |
| 33100 | yes | 0.3 |
| 34000 | no | 4.8 |
| 34100 | yes | 45.0 |
| 44000 | no | 3.3 |
| 44100 | yes | 37.7 |
| 45000 | no | 0.3 |
| 45100 | yes | 0.2 |
| 54100 | yes | 7.0 |
| 54110 | yes | 0.3 |
| 54101 | yes | 0.2 or 0 |
| 54120 | yes | 0.3 |

The analytical results of the carbohydrate chains of three batches of the defucosylated Claudin18.2 antibodies (18.2-A1 and 18.2-A4) generated in the CHO-K1 cells with Fut8 gene knockout are shown in Table 6.

TABLE 6

| Analytical results of carbohydrate chains of the defucosylated 18.2-A1 and 18.2-A4 antibodies | | | | |
|---|---|---|---|---|
| Glycosyl Numbering | Fucose | percentage % 18.2-A1 (Batch 1) | percentage % 18.2-A1 (Batch 2) | percentage % 18.2-A4-1 |
| 33000 | No | 0.7 | 0.8 | 0.60 |
| 34000 | No | 59.9 | 64.9 | 57.9 |
| 43000 | No | 0.6 | 0.4 | 0.83 |
| 44000 | No | 33.1 | 29.1 | 30.9 |
| 45000 | No | 0.4 | 0.4 | 0.1 |
| 54000 | No | 4.3 | 3.0 | 7.1 |
| 54010 | No | 0.3 | 0.2 | 0.8 |
| 54001 | No | 0.2 | 0.1 | 0.1 |
| 54020 | No | 0.2 | 0.2 | 0.5 |

Based on the above results, it was shown that 91.0% of the glycosyl structure of the common Claudin18.2 antibodies produced in CHO-K1 cells contained fucose. In contrast, the three batches of defucosylated Claudin18.2 antibodies produced in the CHO-K1 cells with Fut8 gene knockout contained essentially no detectable fucose in their glycosyl groups.

Example 10. Tests for the Binding Activity of Defucosylated Antibodies

Figure 7:
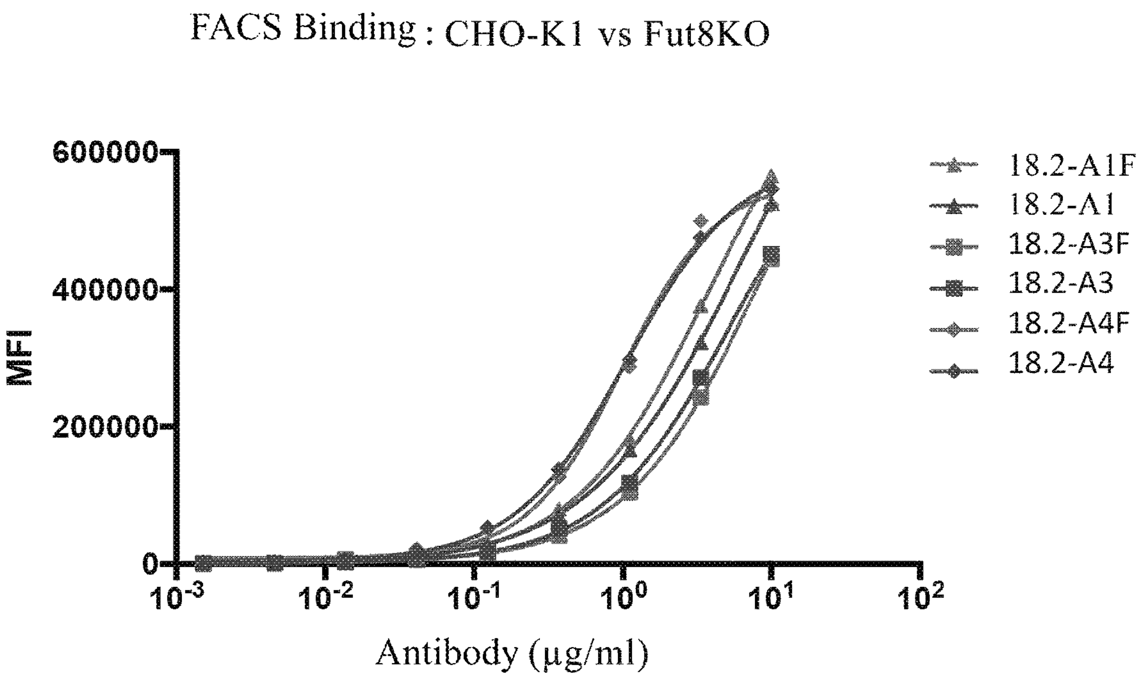
FIG. 7 shows the results of the binding of the CLDN18.2 antibodies and defucosylated antibodies to CT26-CLDN18.2 cells, as tested by flow cytometry.

The binding activity of the defucosylated antibodies 18.2-A1F, 18.2-A3F and 18.2-A4F to CLDN18.2 as compared to the binding activity of 18.2-A1, 18.2-A3 and 18.2-A4 to CLDN18.2 was tested by flow cytometry, the method of which is as described in Example 5, and the experimental results are shown in FIG. 7.

The results showed that there was no significant difference in the biological binding activity of the defucosylated CLDN18.2 antibodies and the common antibodies to CLDN18.2.

Example 11. Tests for the Binding Activity of CLDN18.2 Antibodies and their Defucosylated Forms to FcγRIIIa Subsequently, the binding activity of the CLDN18.2 antibody and its defucosylated form to FcγRIIIa was tested using the Biacore method. Specifically, FcγRIIIa (Sino Biological Inc, 10389-H08C1) was diluted to 0.1 μg/ml in HBS-EP buffer as a ligand, and 18.2-A1F and 18.2-A1 antibody samples were diluted to 360 μg/ml, 120 μg/ml, 40 μg/ml, 13.3 μg/ml and 4.4 μg/ml respectively as analytes. The ligand FcγRIIIa was immobilized using an indirect capture method. First, 50 μg/ml of Anti-His IgG was covalently bound to the surface of CMS chip through amino coupling, followed by the binding of the ligand and analyte. Affinity analysis experiments were performed in Biacore Wizard mode using a multi-cycle approach with FcγRIIIa as the ligand and 18.2-A1F and 18.2-A1 antibody samples as analytes.

The test for each sample includes three Start up, one zero concentration control, five gradient concentration samples and one replicate sample (reference). The chip was regenerated with 10 mM glycine-HCl, pH 1.5 regeneration solution after each cycle. Each concentration cycle of the analyte was set with a capture time of 60 s and a flow rate of the ligand solution of 10 μl/min; a binding time of ligand and analyte of 180 s, and a flow rate of the analyte solution of 30 μl/min; and a dissociation time of 180 s. The CMS chip coupled with Anti-His IgG was placed in the slot for detection and analysis. The raw data were imported into the BIACORE™ X100 analysis software with the value of zero concentration control subtracted, and the value of reference channel was subtracted to eliminate the volume effect, and the affinity analysis method was used to fit the graph in steady-state mode and sort the data.

Figure 8:
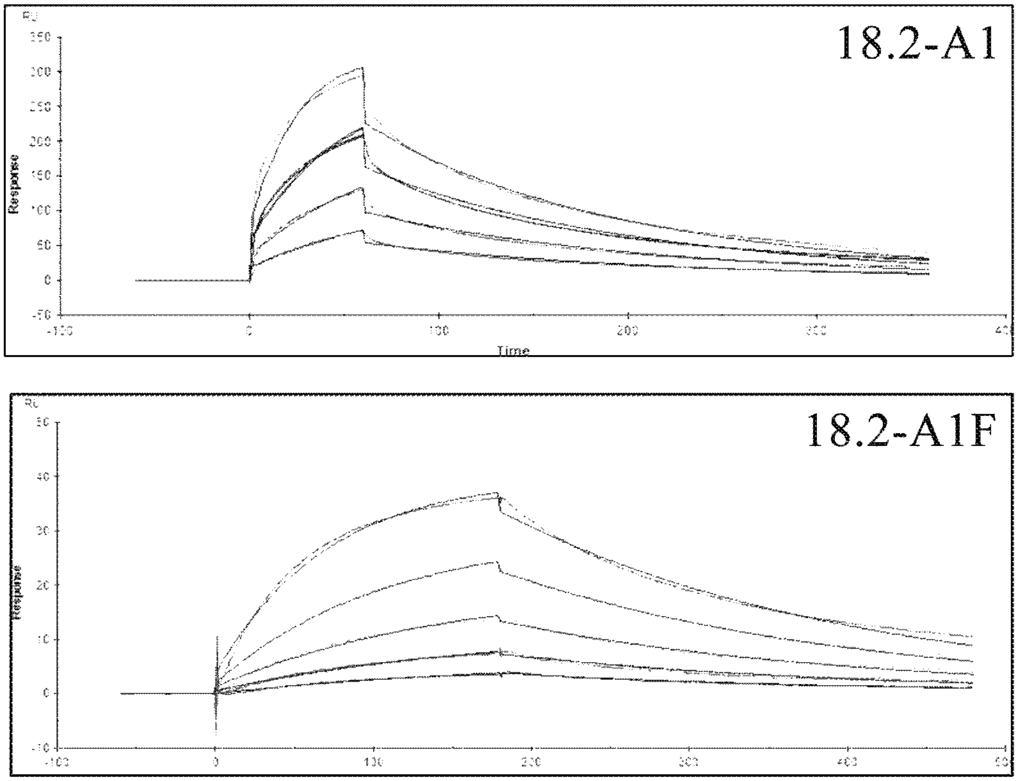
FIG. 8 shows the results of the binding of CLDN18.2-A1 and CLDN18.2-A1F to FcγRIIIa, as tested by Biacore method.

As can be seen from the results in FIG. 8, both the 18.2-A1 antibody and its defucosylated form 18.2-A1F were able to bind to FcγRIIIa effectively. The KD value of the binding of 18.2-A1F antibody to FcγRIIIa was significantly lower than that of the 18.2-A1 antibody. This result indicated that the binding activity of the defucosylated 18.2-A1F antibody to FcγRIIIa was significantly enhanced.

Example 12. Tests for the Binding Activity of CLDN18.2 Antibodies and its Defucosylated Form to FcγRIIIa on the Cell Surface We next further tested the binding activity of the CLDN18.2 antibodies and their defucosylated forms to FcγRIIIa expressed on the cell surface. Specifically, the human FcγRIIIa (V158, high FC binding subtype) gene was cloned into a mammalian cell expression vector carrying a puromycin screening marker and transfected into a Jurkat cell line. A cell line stably expressing FcγRIIIa (FcγRIIIa-Jurkat) was screened with puromycin. In addition, NK92MI is a human NK cell line that naturally expresses the FcγRIIIa receptor (F158, low FC binding subtype). The binding ability of the CLDN18.2 antibodies and their defucosylated forms to FcγRIIIa expressed on the surface of FcγRIIIa-jurkat cells and NK92MI cells was tested by flow cytometry. The specific flow cytometry assay is described with reference to Example 6.

Figure 9:
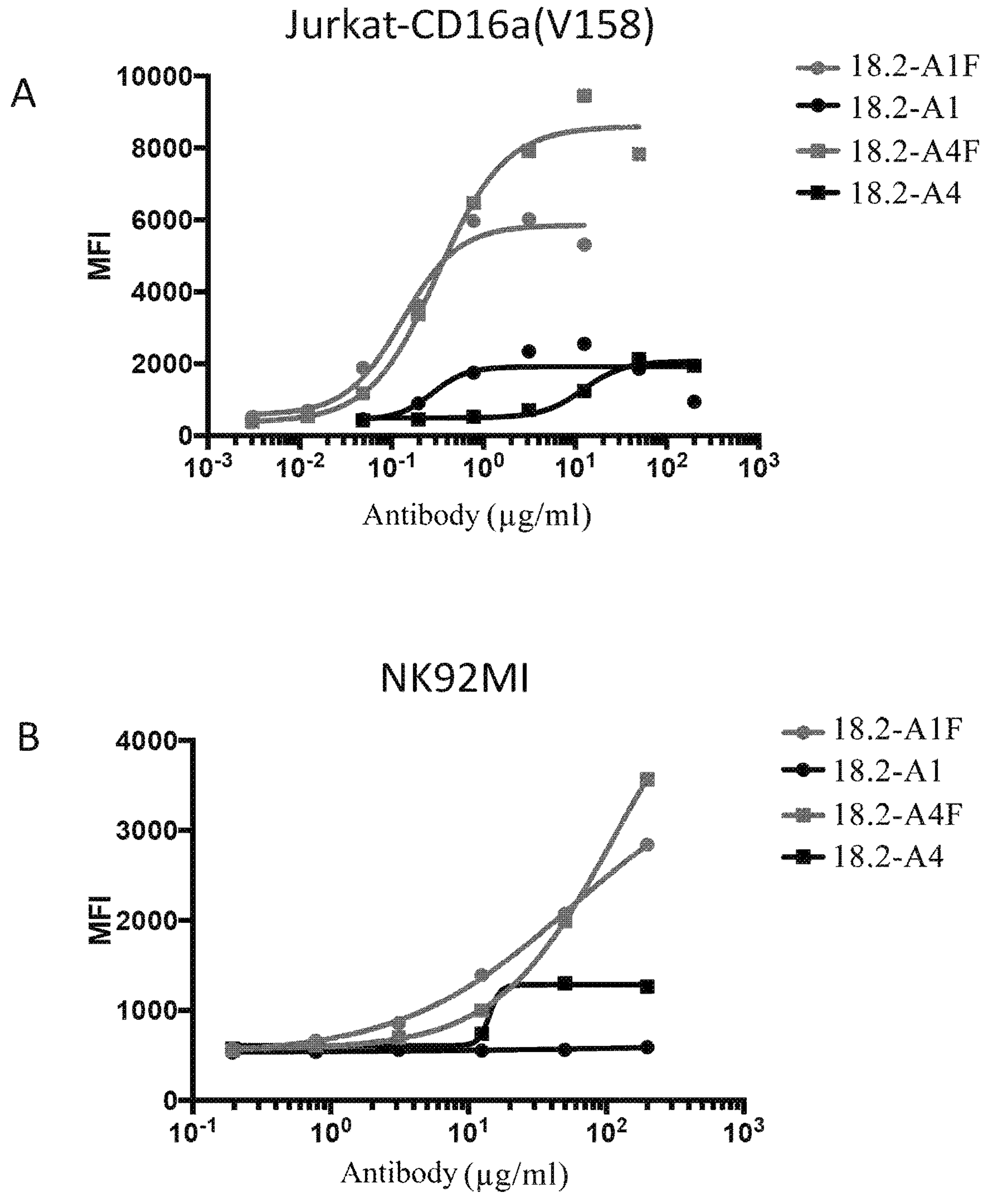
FIG. 9 shows the results of the binding of the CLDN18.2 antibodies and defucosylated antibodies to FcγRIIIa expressed on the cell surface as tested by flow cytometry.

The results of the flow cytometry are shown in FIG. 9. Both the CLDN18.2 antibodies, 18.2-A1 and 18.2-A4, and their defucosylated forms, 18.2-A1F and 18.2-A4F, were able to bind to FcγRIIIa-jurkat cells but were not able to bind to the untransfected Jurkat cells (results not shown). Moreover, the defucosylated 18.2-A1F and 18.2-A4F antibodies were able to better bind to FcγRIIIa-Jurkat cells and NK92MI cells with significantly smaller EC50 than the CLDN18.2 antibodies 18.2-A1 and 18.2-A4 antibodies. The above results indicated that the defucosylated CLDN18.2 antibodies had significantly improved ability in binding to the Fc receptor FcγRIIIa.

Example 13. Activation of FcγRIIIa Receptor by CLDN18.2 Antibodies and their Defucosylated Forms The FcγRIIIa receptor is able to activate the NF-AT transcription factor pathway in effector cells upon binding to the FC region of the antibody. Thus, detection of the NF-AT-mediated reporter gene intensity can reflect the intensity of FcγRIIIa receptor activation. In this example, a promoter containing the NF-AT binding site was inserted in a luciferase reporter gene expression vector and stably transfected into a Jurkat cell line. At the same time, high FC binding FcγRIIIa (V158) was also stably transfected into Jurkat cells, thereby constructing a functional cell line that can sense the intensity of FcγRIIIa receptor activation (FcγRIIIa-Jurkat).

SNU601 gastric cancer cells stably expressing CLDN18.2 (SNU601-CLDN18.2) were taken, diluted to $4\times10^5$/ml, and mixed with FcγRIIIa-Jurkat cells in a ratio of 1:6. 100 μl of the mixed cells were added to a 96-well plate, followed by the addition of fold-diluted antibodies, respectively, and incubated statically at 37° C. for 6 h. Subsequently, the luciferase activity was tested with the One-Glo kit (promega).

Figure 10:
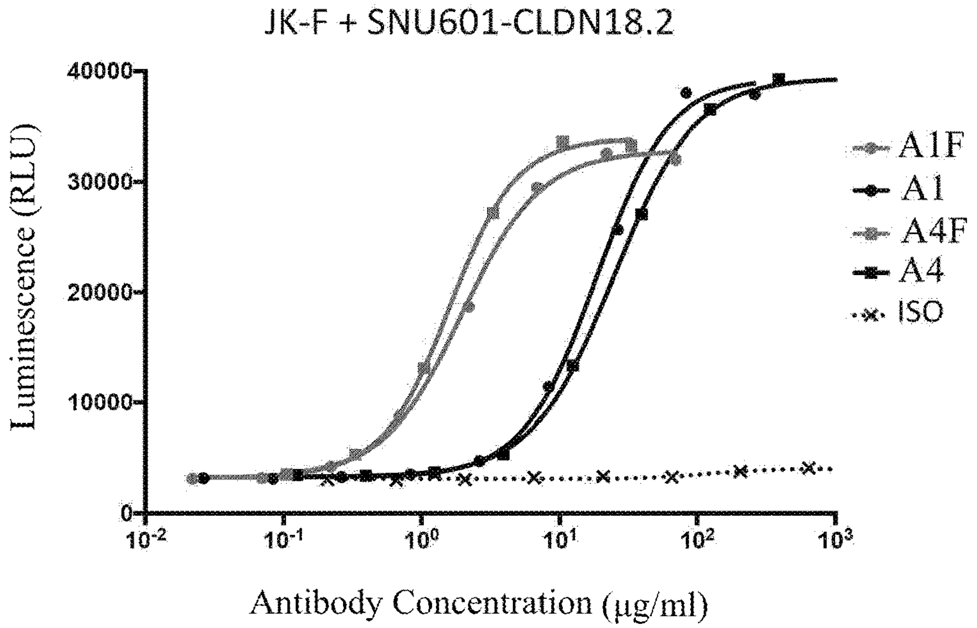
FIG. 10 shows the results of the activation of FcγRIIIa receptors in FcγRIIIa-Jurkat cells by the CLDN18.2 antibodies and defucosylated antibodies in the presence of SNU601-CLDN18.2 cells (FIG. 10A) or CT26-CLDN18.2 (FIG. 10B), as tested by Luciferase reporting system.
Figure 10:
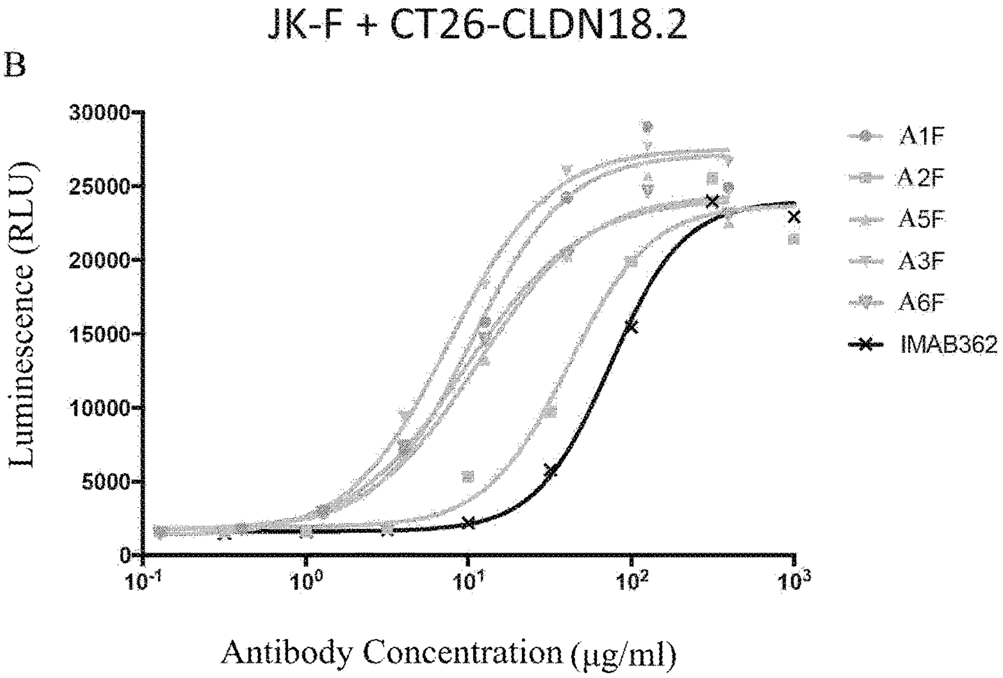

The results are shown in FIG. 10. As compared to the 18.2-A1 and 18.2-A4 antibodies produced in CHO-K1 cells, the antibodies 18.2-A1F and 18.2-A4F expressed in the CHO cell line with Fut8 gene knockout induced a significant increase in FcγRIIIa receptor activity with approximately 10 to 20-fold higher of the EC50 values.

Example 14. Enhancement of CLDN18.2 Antibody Induced FcγRIIIa Receptor Activation by the Combined Chemotherapeutic Drug EOF Combined chemotherapy regimen including EOF (Epirubicin; Oxaliplatin; 5-FU) is the main available treatment method for gastric cancer. EOF-sensitive cell lines undergo varying degrees of cell division cycle blockade, proliferation inhibition and apoptosis after EOF treatment.

Figure 11:
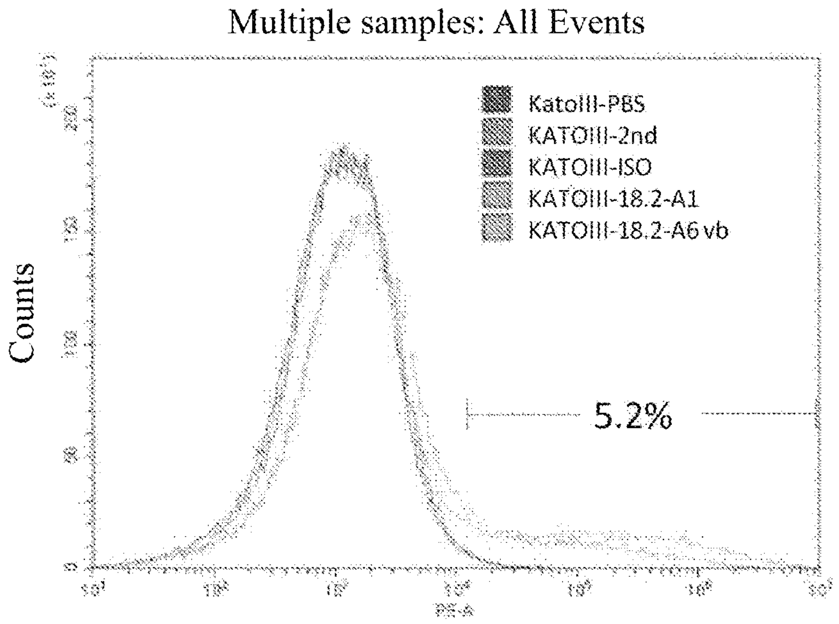
FIG. 11 shows the results of CLDN18.2 expression level on KATOIII cells as tested by flow cytometry.
Figure 12A:
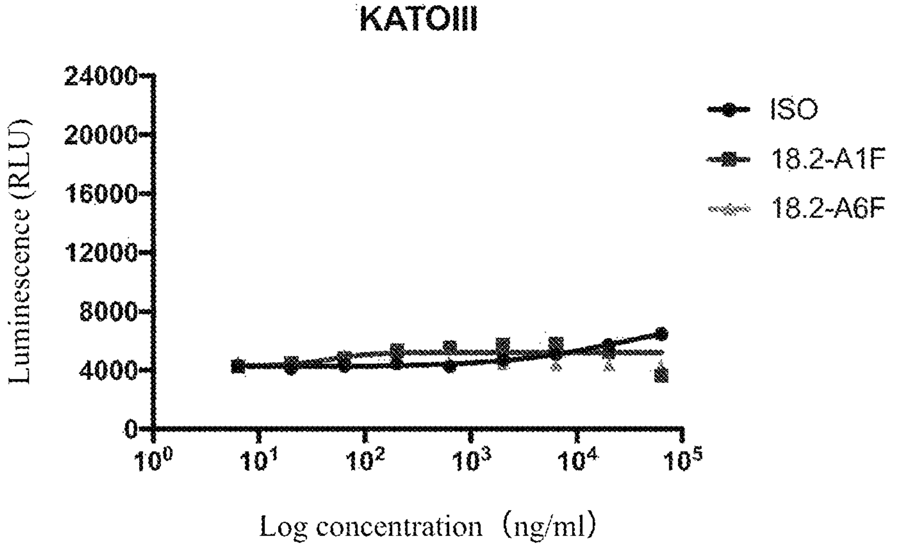
FIG. 12 shows the results of the activation of FcγRIIIa receptors in FcγRIIIa-Jurkat cells by the CLDN18.2 antibodies (FIG. 12A) and the combination of the CLDN18.2 antibodies with the chemotherapeutic drug EOF (FIG. 12B) in the presence of SNU601-CLDN18.2 cells, as tested by Luciferase reporting system.

KATOIII cells are a human gastric epithelial cancer cell line that expresses a very low level of CLDN18.2, with only about 5.2% of cells showing significant positivity in flow cytometry (FIG. 11). Due to the low level of CLDN18.2 expression, in the antibody-induced FcγRIIIa receptor activation experiment with the KATOIII cells and FcγRIIIa-Jurkat cells co-incubated (experimental method as described in Example 13), the 18.2-A1F and 18.2-A6F antibodies did not cause FcγRIIIa receptor activation (FIG. 12A).

Figure 12B:
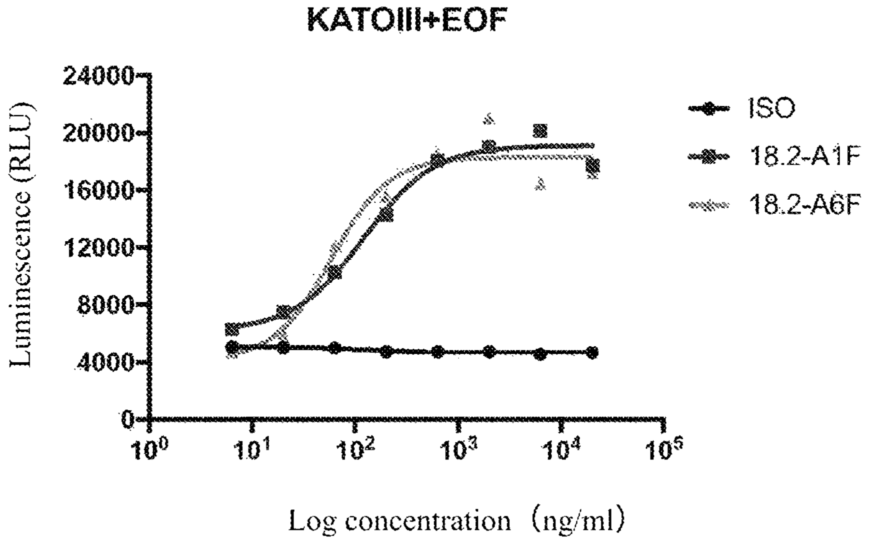

Further, after KATOIII cells were treated with sublethal doses of EOF (Epirubicin: 300 nM; Oxaliplatin: 130 nM; 5-fluorouracil: 561.3 nM) for 48 h, microscopic observation and flow cytometry revealed an increase in cell volume, rounding and a decrease of cells at division phase. It was indicated that the cells stayed in the division phase. However, the cells remained alive and did not show obvious apoptosis (results not shown). The EOF-treated KATOIII cells were co-incubated with FcγRIIIa-Jurkat cells and CLDN18.2 antibodies of different concentrations. The results showed that the 18.2-A1F and 18.2-A6F antibodies can induce significant FcγRIIIa receptor activation as compared to the isotype control (ISO) (FIG. 12B).

The above results indicated that the currently commonly used chemotherapeutic drug EOF had an inhibitory effect on the growth of gastric cancer cells. Following the treatment with EOF, it enhanced the CLDN18.2 antibody-induced FcγRIIIa receptor activation. Without wishing to be bound by theory, the effect may be due to the treatment with the chemotherapeutic drug promoting the ADCC effect of CLDN18.2 antibodies through up-regulation of antigen expression on cells and other mechanisms.

Example 15. Killing of CLDN18.2-Expressing Tumor Cells by the Antibodies

Peripheral blood leukocytes (PBMC) from healthy human (donor 1 and donor 2) were isolated with Ficoll-Paque Plus (GE Healthcare) and cultured overnight at 37° C. SNU601 gastric cancer cells stably expressing CLDN18.2 (SNU601-CLDN18.2) were taken and diluted to $1\times10^5$/ml, and PBMC were diluted to $5\times10^6$/ml, the two were mixed in equal volumes with a ratio of 50:1 of effector cells to target cells. 100 μl of the mixed cells were added to a 96-well plate, and then the fold-diluted antibodies were added separately and incubated statically at 37° C. for 24 hours. Subsequently, cell viability was tested using the lactate dehydrogenase (LDH) assay (promega), which determines the absorbance at OD490 by microplate reader. The killing rate was calculated as follows:

Minimum release group: single cultivation of target cells

Maximum release group: target cells+lysate

Experimental group: target cells+effector cells+CLDN18.2 antibody

Control group: target cells+effector cells+negative control antibody $$\text{Killing rate (\%)} = (\text{experimental group} - \text{minimum release group}) / (\text{maximum release group} - \text{minimum release group}) \times 100\%$$

Figure 13:
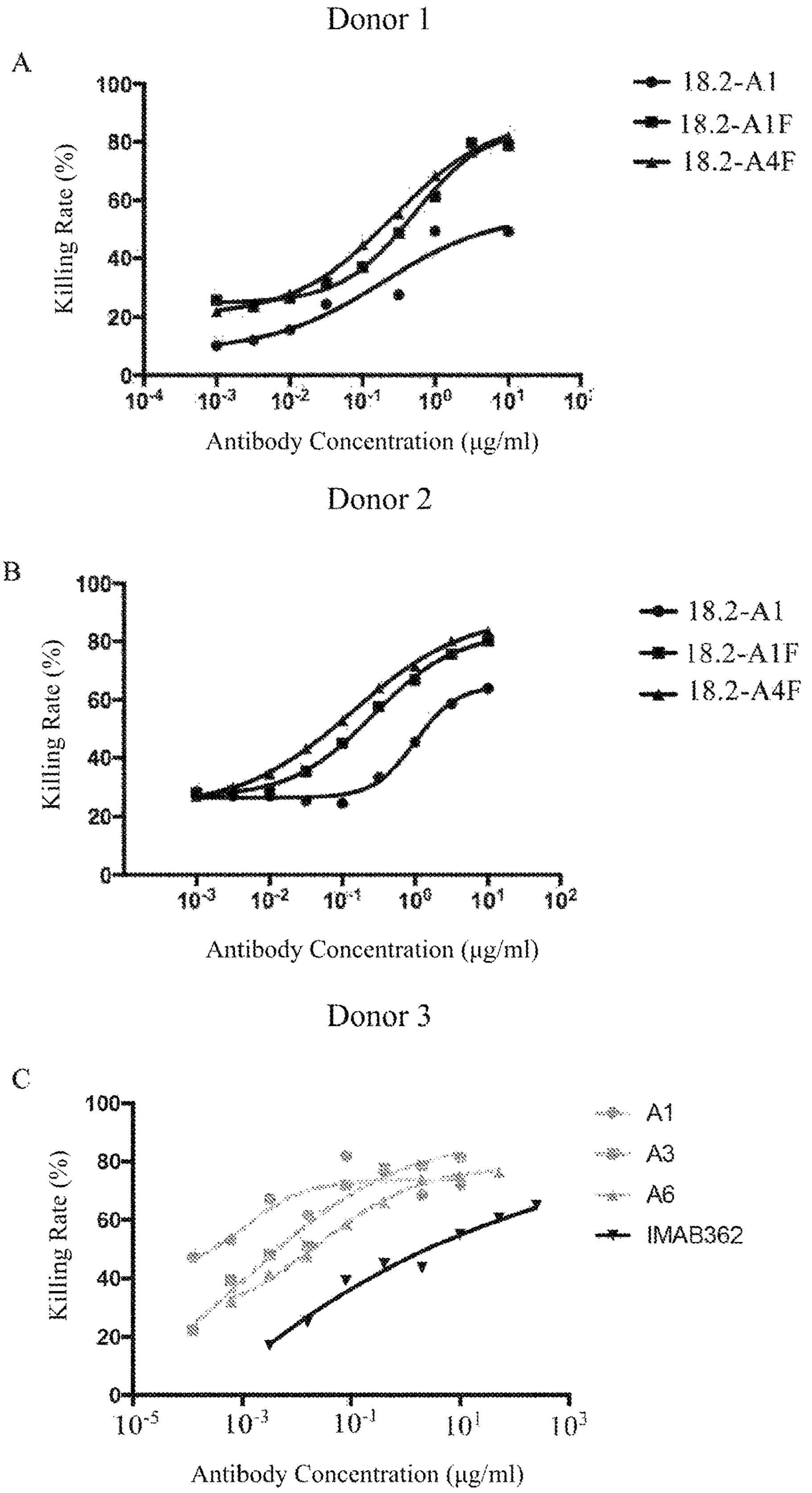
FIG. 13 shows the killing effect of the ADCC pathway mediated by the CLDN18.2 antibodies and the defucosylated antibodies on SNU601-CLDN18.2 target cells in the presence of PBMCs from healthy human Donor 1 (FIG. 13A), Donor 2 (FIG. 13B) or Donor 3 (FIG. 13C).

The results are shown in FIG. 13. The negative control antibody did not show significant cell killing (results not shown), and all the CLDN18.2 antibody 18.2-A1 and the defucosylated antibodies 18.2-A1F and 18.2-A4F were able to effectively cause the death of target cells expressing CLDN18.2, and their maximum killing rates could reach 80-90%. In addition, by comparing the defucosylated antibodies with the common antibodies, the maximum killing rate towards target cells and IC50 values of the defucosylated antibodies were significantly higher than those of the common antibodies.

Example 16. CDC Activity of the CLDN18.2 Antibodies

HELA cells stably expressing CLDN18.2 were taken and resuspended in medium containing 1% serum with inactivated complement, and were counted, and the cell concentration was adjusted to $2\times10^5$/ml with cell viability greater than 90%. 50 μl of cells per well were added in a 96-well plate, followed by the addition of fold-diluted antibodies respectively and 50 μl of diluted human serum. The cells were incubated at 37° C. for 2 hours. Subsequently, the cell lysis rate was measured by the CCK8 method. The cell lysis rate was calculated as follows:

Minimum release group: target cells

Maximum release group: target cells+lysate

Experimental group: target cells+CLDN18.2 antibody+complement

Negative control group: target cells+negative control antibody+complement $$\text{Killing rate (\%)} = (\text{experimental group} - \text{minimum release group}) / (\text{maximum release group} - \text{minimum release group}) \% \times 100\%$$

Figure 14:
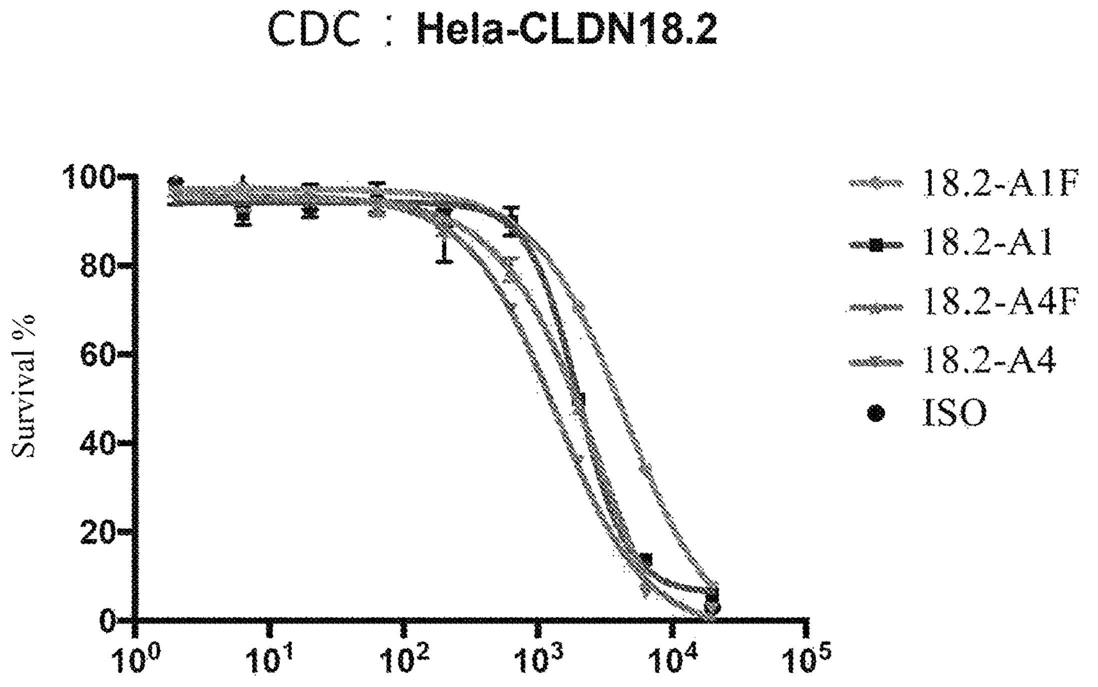
FIG. 14 shows the killing effect of the CDC pathway mediated by the CLDN18.2 antibodies and the defucosylated antibodies on CHO-CLDN18.2 target cells in the presence of complements.

The results are shown in FIG. 14. All the CLDN18.2 antibodies 18.2-A1 and 18.2-A4 and their defucosylated forms 18.2-A1F and 18.2-A4F had significant CDC activity, with a maximum killing rate of >95% against target cells. In addition, there was no significant difference in the CDC activity between the defucosylated form of antibodies and the normal antibodies.

Example 17. In Vivo Tumor Killing Activity of CLDN18.2 Antibody

A mouse xenograft model of SNU601 cells was established by subcutaneous inoculation of NPG immunodeficient mice with SNU601-CLDN18.2 cells and Ficoll isolated human PBMC cells (SNU601-CLDN18.2 cells: PBMC is 1:0.8). Subsequently, NPG immunodeficient mice inoculated with SNU601 tumor cells were injected intraperitoneally with 18.2-A1F antibody 18.2-A1F at a dose of 10 mg/kg or 5 mg/kg, or blank control (PBS) or IgG isotype control (ISO), n=15 mice per group. Drugs were administered every 3 days after tumor inoculation, and the volume of tumors in mice was measured.

Figure 15:
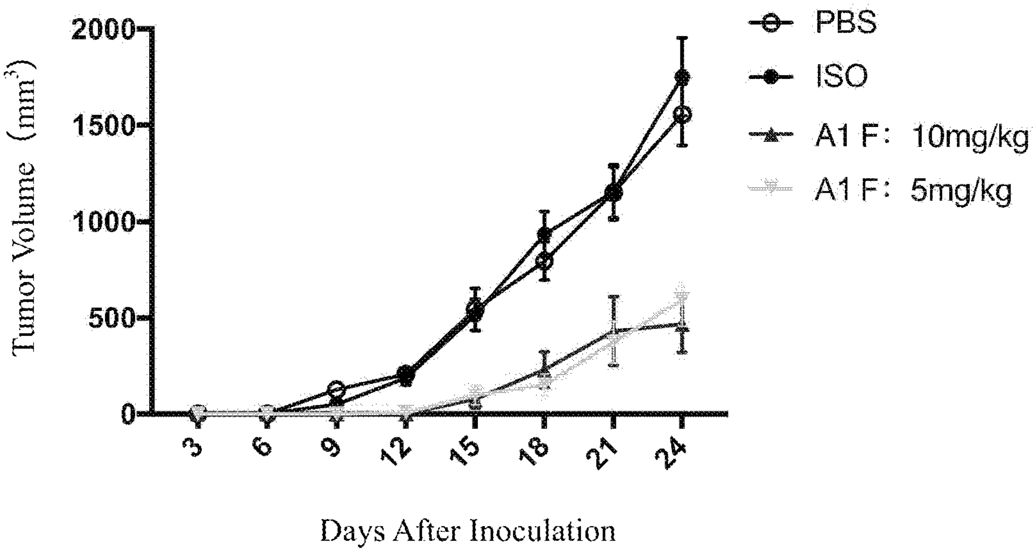
FIG. 15 shows the results of tumor growth inhibition by different doses of the CLDN18.2 antibody 18.2-A1F in a mouse xenograft model of SNU601-CLDN18.2 cells.

As shown by the results in FIG. 15, the 18.2-A1F antibody treatment groups at the doses of 5 mg/kg and 10 mg/kg showed good tumor suppression effects as compared to the PBS group and the IgG isotype control antibody group, and there was no obvious effect difference between the 5 mg/kg and 10 mg/kg groups.

Figure 16:
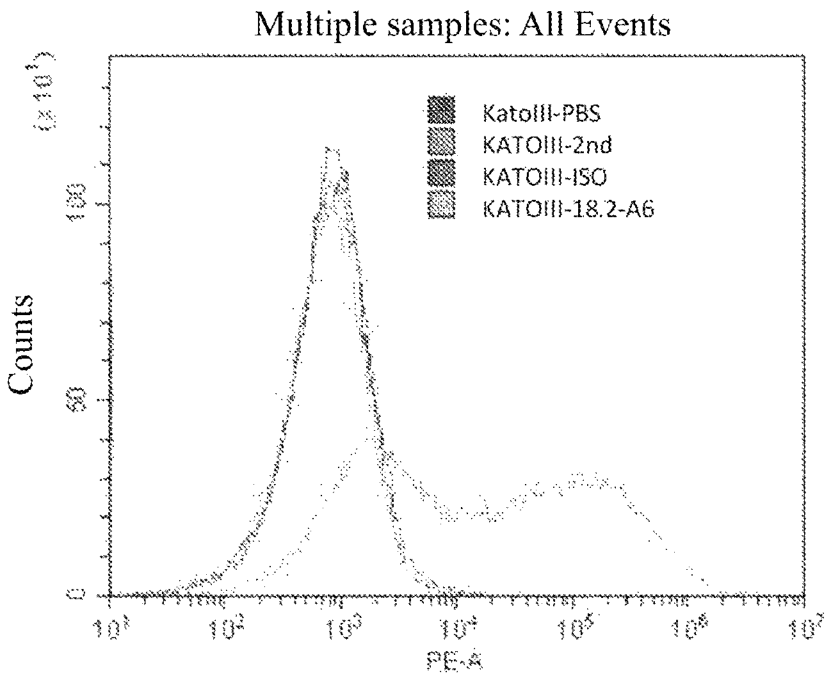
FIG. 16 shows the flow cytometry results of CLDN18.2 highly expressed KATOIII cells (KATOIII-18.2High) used in a xenograft model.

Example 18. In Vivo Tumor Killing Activity of the Combination of CLDN18.2 Antibody and Chemotherapeutic Drug As shown by the results in Example 14, in vitro EOF combined chemotherapy was capable of increasing CLDN18.2 antibody induced FcγRIIIa receptor activation. KATOIII expressed a very low level of CLDN18.2 when cultured in vitro in IMDM medium, with only about 5.2% of the cells showing obvious positivity in flow cytometry (FIG. 11). After flow cytometry sorting, KATOIII cells with high CLDN18.2 expression (KATOIII-18.2High) were selected to inoculate NPG immunodeficient mice for xenograft model experiments (FIG. 16).

A xenograft model of KATOIII-18.2High cells was established by subcutaneously inoculating NPG immunodeficient mice with KATOIII-18.2High cells and Ficoll isolated human PBMC cells (KATOIII-18.2High cells: PBMC is 1:0.8). Subsequently, NPG immunodeficient mice inoculated with KATOIII-18.2High tumor cells were injected intraperitoneally with isotype control antibody (ISO), EOF (Epirubicin: 1 mg/kg; Oxaliplatin: 3 mg/kg; 5-fluorouracil: 30 mg/kg), 10 mg/kg dose of 18.2-A1F antibody, or EOF and 18.2-A1F, n=6 mice per group. Drugs were administered every 3 days after tumor inoculation, and the volume of tumors in mice was measured.

Figure 17:
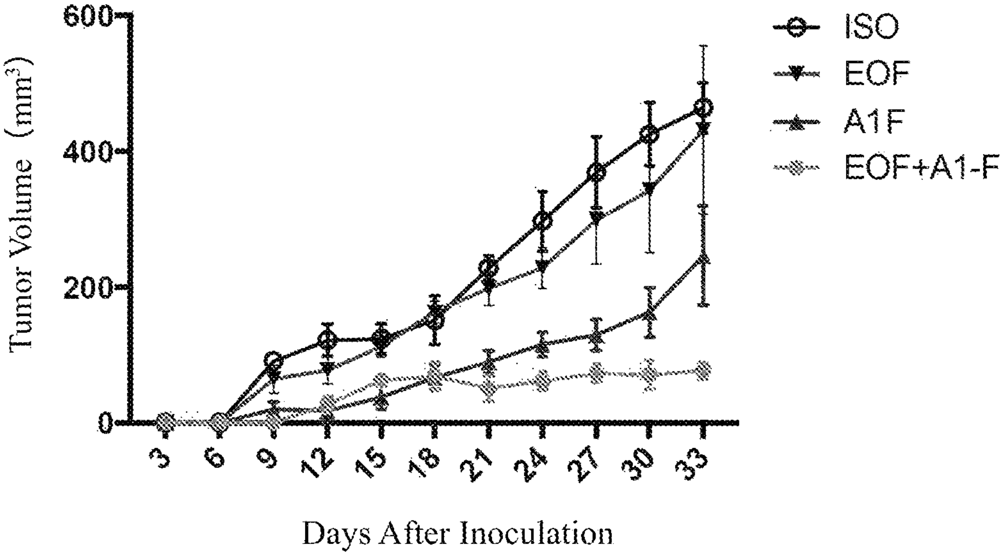
FIG. 17 shows the results of tumor growth inhibition by the CLDN18.2 antibody 18.2-A1F and the combination of 18.2-A1F with the chemotherapeutic drug EOF in a mouse xenograft model of KATOIII-18.2High cells.

As shown by the results in FIG. 17, 18.2-A1F is capable of effectively inhibiting tumor growth as compared to the EOF group and the control antibody group, and the combination of 18.2-A1F with EOF further significantly reduced tumor growth, which indicated the potential of the combination of 18.2-A1F with chemotherapy in the clinical treatment of cancers.

The invention claimed is:

1. An antibody that binds to CLDN18.2, or an antigen-binding fragment thereof, wherein the antibody or the antigen-binding fragment thereof comprises a heavy chain variable region (VH) comprising heavy chain CDRs (CDRHs) and a light chain variable region (VL) comprising light chain CDRs (CDRLs), wherein the CDRHs and the CDRLs are selected from the group consisting of:

a. CDRH1, CDRH2 and CDRH3 as shown in SEQ ID NOs: 3-5; and CDRL1, CDRL2 and CDRL3 as shown in SEQ ID NOs: 8-10;

b. CDRH1, CDRH2 and CDRH3 as shown in SEQ ID NOs: 13-15; and CDRL1, CDRL2 and CDRL3 as shown in SEQ ID NOs: 18-20;

c. CDRH1, CDRH2 and CDRH3 as shown in SEQ ID NOs: 23-25; and CDRL1, CDRL2 and CDRL3 as shown in SEQ ID NOs: 28-30;

d. CDRH1, CDRH2 and CDRH3 as shown in SEQ ID NOs: 33-35; and CDRL1, CDRL2 and CDRL3 as shown in SEQ ID NOs: 38-40;

e. CDRH1, CDRH2 and CDRH3 as shown in SEQ ID NOs: 43-45; and CDRL1, CDRL2 and CDRL3 as shown in SEQ ID NOs: 48-50; and f. CDRH1, CDRH2 and CDRH3 as shown in SEQ ID NOs: 57-59; and CDRL1, CDRL2 and CDRL3 as shown in SEQ ID NOs: 62-64.

2. The antibody or antigen-binding fragment thereof of claim 1, wherein the antibody has the following VH and VL:

a. a VH comprising the amino acid sequence of SEQ ID NO: 1, and a VL comprising the amino acid sequence of SEQ ID NO: 6;

b. a VH comprising the amino acid sequence of SEQ ID NO: 11, and a VL comprising the amino acid sequence of SEQ ID NO: 16;

c. a VH comprising the amino acid sequence of SEQ ID NO: 21, and a VL comprising the amino acid sequence of SEQ ID NO: 26;

d. a VH comprising the amino acid sequence of SEQ ID NO: 31, and a VL comprising the amino acid sequence of SEQ ID NO: 36;

e. a VH comprising the amino acid sequence of SEQ ID NO: 41, and a VL comprising the amino acid sequence of SEQ ID NO: 46; or f. a VH comprising the amino acid sequence of SEQ ID NO: 55, and a VL comprising the amino acid sequence of SEQ ID NO: 60.

3. The antibody or antigen-binding fragment thereof of claim 1, wherein the antibody has an Fc region.

4. The antibody or antigen-binding fragment thereof of claim 3, wherein the antibody has a glycosyl structure modification at Asn297, wherein the numbering is according to the EU numbering system.

5. The antibody or antigen-binding fragment thereof of claim 4, wherein the ratio of glycosyl structures having fucose to total glycosyl structures is 50% or less.

6. The antibody or antigen-binding fragment thereof of claim 5, wherein the ratio of glycosyl structures having fucose to total glycosyl structures is 0%-1%.

7. The antibody or antigen-binding fragment thereof of claim 5, wherein the antibody is produced by a cell with Fut8 gene knockout.

8. The antibody or antigen-binding fragment thereof of claim 1, wherein the antibody is a monoclonal antibody, a bispecific antibody or a multispecific antibody.

9. The antibody or antigen-binding fragment thereof of claim 1, wherein the antibody is selected from a group consisting of IgG, IgA, IgM, IgE, and IgD isotypes.

10. The antibody or antigen-binding fragment thereof of claim 1, wherein the antibody is selected from a group consisting of IgG1, IgG2, IgG3, and IgG4 subclasses.

11. The antibody or antigen-binding fragment thereof of claim 1, wherein the antigen-binding fragment is selected from a group consisting of Fab fragment, Fab' fragment, $F(ab')_2$ fragment, Fd fragment, Fd' fragment, Fv fragment, scFv fragment, ds-scFv fragment, dAb fragment, single chain fragment, diabody and linear antibody.

12. A nucleic acid molecule comprising a nucleotide sequence encoding the antibody or antigen-binding fragment thereof of claim 1.

13. A conjugate comprising the antibody or antigen-binding fragment thereof of claim 1 conjugated to a therapeutic agent, a diagnostic agent or an imaging agent.

14. A composition comprising the antibody or antigen-binding fragment thereof of claim 1 and one or more pharmaceutically acceptable carriers, excipients and/or diluents.

15. The composition of claim 14, wherein the composition further comprises one or more additional therapeutic agents selected from a group consisting of antibody, chemotherapeutic, and small molecule drug.

16. The composition of claim 15, wherein the chemotherapeutic is selected from one or more of epirubicin, oxaliplatin, and 5-fluorouracil (5-FU).

17. A method for treating a cancer associated with the expression of CLDN18.2 in a subject, wherein the method comprises a step of administering to the subject the antibody or antigen-binding fragment thereof of claim 1.

18. The method of claim 17, wherein the cancer is selected from a group consisting of gastric cancer, cholangiocarcinoma, esophageal cancer, and pancreatic cancer.

19. The method of claim 17, wherein the method further comprises a step of administering one or more additional therapies to the subject.

20. The method of claim 19, wherein the additional therapy is selected from a group consisting of chemotherapy, radiation therapy, immunotherapy, and surgery.

21. The method of claim 20, wherein the immunotherapy is selected from a group consisting of therapy targeting an immune checkpoint molecule, CAR-T cell therapy, and CAR-NK cell therapy.

22. The method of claim 20, wherein the chemotherapy is selected from a combined chemotherapy regimen comprising epirubicin, oxaliplatin, and 5-fluorouracil.

23. An antibody that binds to CLDN18.2, or an antigen-binding fragment thereof, wherein the antibody or the antigen-binding fragment thereof comprises a heavy chain variable region (VH) comprising the amino acid sequence of SEQ ID NO: 1 and a light chain variable region (VL) comprising the amino acid sequence of SEQ ID NO: 6.

24. A method for treating a cancer associated with the expression of CLDN18.2 in a subject, wherein the method comprises a step of administering to the subject the antibody or antigen-binding fragment thereof of claim 23.

* * * * *